(12) United States Patent
Honda et al.

(10) Patent No.: US 9,132,195 B2
(45) Date of Patent: Sep. 15, 2015

(54) CELLULOSE POWDER HAVING EXCELLENT SEGREGATION PREVENTIVE EFFECT, AND COMPOSITIONS THEREOF

(75) Inventors: Yosuke Honda, Tokyo (JP); Kazuhiro Oobae, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 500 days.

(21) Appl. No.: 12/993,580

(22) PCT Filed: May 21, 2009

(86) PCT No.: PCT/JP2009/059318
§ 371 (c)(1),
(2), (4) Date: Nov. 19, 2010

(87) PCT Pub. No.: WO2009/142255
PCT Pub. Date: Nov. 26, 2009

(65) Prior Publication Data
US 2011/0062630 A1    Mar. 17, 2011

(30) Foreign Application Priority Data

May 21, 2008 (JP) ................................. 2008-132817

(51) Int. Cl.
| | | |
|---|---|---|
| *A61K 9/20* | (2006.01) | |
| *A61K 47/38* | (2006.01) | |
| *A23L 1/0534* | (2006.01) | |
| *A61K 8/73* | (2006.01) | |
| *C08J 3/12* | (2006.01) | |
| *C08L 1/02* | (2006.01) | |
| *A61K 51/12* | (2006.01) | |
| *A61K 9/14* | (2006.01) | |

(52) U.S. Cl.
CPC ............... *A61K 47/38* (2013.01); *A23L 1/0534* (2013.01); *A61K 8/731* (2013.01); *A61K 9/2054* (2013.01); *C08J 3/12* (2013.01); *C08L 1/02* (2013.01); *A23V 2002/00* (2013.01); *A61K 9/14* (2013.01); *A61K 9/2095* (2013.01); *A61K 51/1241* (2013.01); *C08J 2301/02* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 4,159,345 A | 6/1979 | Takeo et al. | |
| 5,417,984 A * | 5/1995 | Banker et al. | 424/488 |
| 5,804,217 A | 9/1998 | Bjork et al. | |
| 2004/0043964 A1 | 3/2004 | Gomi et al. | |
| 2004/0053887 A1 | 3/2004 | Obae et al. | |
| 2007/0190017 A1 | 8/2007 | Yamasaki et al. | |
| 2008/0019883 A1* | 1/2008 | Fike et al. | 422/139 |
| 2009/0022791 A1* | 1/2009 | Obae et al. | 424/464 |
| 2010/0178331 A1* | 7/2010 | Nagata et al. | 424/451 |

FOREIGN PATENT DOCUMENTS

| | | |
|---|---|---|
| JP | 53-127553 | 11/1978 |
| JP | 54-62328 | 5/1979 |
| JP | 63-267731 | 11/1988 |
| JP | 8-510766 | 11/1996 |
| JP | 2003-81876 | 3/2003 |
| WO | 02/02643 | 1/2002 |
| WO | 02/36168 | 5/2002 |
| WO | 2005/073286 | 8/2005 |
| WO | 2006/115198 | 11/2006 |
| WO | WO 2006115198 A1 * | 11/2006 |
| WO | WO 2008078730 A1 * | 7/2008 |
| WO | 2008/149894 | 12/2008 |

OTHER PUBLICATIONS

International Search Report for PCT/JP2009/059318, mailed Sep. 1, 2009.

* cited by examiner

*Primary Examiner* — James Rogers
(74) *Attorney, Agent, or Firm* — Greenblum & Bernstein, P.L.C.

(57) ABSTRACT

With regard to compositions derived from active ingredients and other additives in medical, food and industrial fields, there have been problems that the active ingredients cannot be uniformly mixed, and that the active ingredients become segregated and lose uniformity as the active ingredients undergo transport, input, and filling processes. There is provided a cellulose powder which improves the uniformity of compositions containing active ingredients or other additives to prevent segregation of the active ingredients, wherein the cellulose powder contains cellulose I type crystals, has an average particle diameter of less than 30 μm, a powder density of 0.1 to 0.45 g/cm$^3$, a tapping density of 0.1 to 0.5 g/cm$^3$, a repose angle of 35 to 50°, a specific surface of more than or equal to 0.1 m$^2$/g and less than 20 m$^2$/g, an internal friction angle of 36 to 42°, and is a cellulose powder including a secondary flocculation structure in which primary particles are flocculated.

10 Claims, 4 Drawing Sheets

CELLULOSE POWDER HAVING EXCELLENT SEGREGATION PREVENTIVE EFFECT, AND COMPOSITIONS THEREOF

This application is a U.S. national stage application of PCT/JP2009/059318, filed May 21, 2009, which claims priority to JP 2008-132817 filed May 21, 2008. The entire disclosure of PCT/JP2009/059318 is incorporated by reference herein in its entirety.

TECHNICAL FIELD

The present invention relates to a cellulose powder useful as a base to prevent the segregation of active ingredients used in the pharmaceutical, health food, food and industrial fields.

BACKGROUND ART

In the pharmaceutical, health food, food and industrial fields, it has conventionally been widely carried out to prepare compositions in each of which an active ingredient is mixed with other additives.

Particularly, many active ingredients used in the pharmaceutical and health food fields have low moldability and thus an excipient is generally used as an additive in preparing compositions such as a tablet, granules, and fine granules. Among them, crystalline cellulose is widely used as an excipient for a tablet since it has high moldability as well as rapid disintegration.

When the content of an active ingredient is 20% by weight or less, its content needs to be made uniform in a tablet in order to accurately exert its pharmaceutical effect. In order to make the content of the active ingredient uniform, a method, such as a wet compression method involving mixing an active ingredient with other additives, granulating the mixture using water or the like together with a binder to make granules, further adding a lubricant and mixing, and compressing this mixture to form a tablet; or a wet granulation and tableting with extra-granular addition of disintegrant involving adding crystalline cellulose and a disintegrant to the above granules and mixing, further adding a lubricant and mixing, and compressing this mixture to form a tablet, is used. In the wet granulation and tableting with extra-granular addition of disintegrant, it is desired that granules containing an active ingredient and other additives such as crystalline cellulose and a disintegrant are not separated or segregated from each other during a mixing step or other steps passed through until forming a tablet.

On the other hand, a direct compression method is known which involves mixing an active ingredient with other additives, further adding a lubricant and mixing, and compressing this mixture to form a tablet. With regard to the direct compression method, it is difficult to ensure the content uniformity compared to the wet compression method and the wet granulation and tableting with extra-granular addition of disintegrant because it does not include any step of processing the active ingredient into granules or the like and is directly affected by the physical properties of the active ingredient. In order to reduce effects of the physical properties of an active ingredient, pulverizing the active ingredient to render its particle size small is carried out. Rendering the particle size of an active ingredient small brings about low fluidity because it reduces the weight and increases the surface adhesion. As a result, since the insufficient filling into a die occurs during tableting, variation of the tablet weight easily arises, and thus it is difficult to ensure the content uniformity of the active ingredient.

Thus, for the direct compression method, it is a challenge to reconcile the stabilization of the physical property of an active ingredient with such fluidity as to enable the tableting thereof. To ensure fluidity, additives having good fluidity are generally added. Most of them have a large average particle size. However, there is a problem that an increase in the difference between the average particle size of the active ingredient and the particle size of the additives facilitates the occurrence of separation and segregation. The following have previously been disclosed as a method for overcoming the separation and segregation.

CITATION LIST

Patent Document

PATENT DOCUMENT 1: JP 2003-81876 A
PATENT DOCUMENT 2: WO 2006-115198 A1
PATENT DOCUMENT 3: JP 63-267731 A
PATENT DOCUMENT 4: JP 54-62328 A
PATENT DOCUMENT 5: JP 53-127553 A
PATENT DOCUMENT 6: PCT/JP 2008/060279 specification
PATENT DOCUMENT 7: WO 02/02643 pamphlet

DISCLOSURE OF THE INVENTION

Problems to be Solved by the Invention

As a method for preventing the reduction of the fluidity of an active ingredient which occurs when the particle size of the active ingredient is controlled to be small by the pulverization or the like, Patent Document 1 discloses a mixing method which involves mixing in advance a drug with a glidant (talc, light anhydrous silicic acid, or the like) and further mixing the powder mixture with other additives to improve the content uniformity of the drug. This document describes that the advantageous effect can be hardly obtained if an amount of these inorganic glidants is over 200% by weight based on the drug because the dustability and adhesion of the glidant arise and thereby reduces workability. The document also describes that a lower concentration of the used drug results in a more remarkable effect. In view of the drug content in Examples of the Patent Document, it is considered that the method is effective when the drug content is 2% or less. Consequently, when the drug content of the composition is 2% or less, it may be difficult to blend these glidants in an amount of more than 4% based on the total weight. According to the document, the additives other than a glidant should be added after a drug is mixed with the glidant in advance, which causes a problem due to such troublesome work in preparation. A glidant containing a metal salt can reduce the stability of a drug and thus has not been necessarily suited to practical use. In addition, when talc is used, care should be taken to ensure safety in handling because talc has the same chemical composition as that of asbestos. In the health food field in Japan, the usage amount of talc is restricted to 0.5% or less. In accordance with the above, there has been a need for an additive which is not restricted in the usage amount, has good handleability, does not affect the stability of an active ingredient, and can improve the content uniformity.

Patent Document 2 describes a porous cellulose aggregate which has a secondary aggregation structure formed by aggregation of primary particles of cellulose; has an intraparticle pore volume of 0.265 cm$^3$/g to 2.625 cm$^3$/g; contains type I crystalline; has an average particle size of greater than 30 μm and less than or equal to 250 μm, a specific surface area of 1.3 to 20 m²/g, and a repose angle of greater than or equal to 25° and less than 44°; and has the property of being disintegrated in water. This document describes that an average particle size of 30 μm or less causes cellulose particles to aggregate with each other and thus makes it less easy to uniformly disperse an active ingredient when mixing with the active ingredient, is liable to increase the variation of the active ingredient in the resulting molded product, and also tends to increase variation of the weight of the molded product in the continued production thereof. Thus, it has been considered difficult to suppress the variation of the active ingredient if the particle size is simply reduced. The document also describes that the porous cellulose aggregate can improve mixing uniformity by holding inside the particle the active ingredient pulverized into 10 μm or less. However, since the aggregability of the active ingredient pulverized into 10 μm or less becomes higher, it has been necessary to use in combination a method for loosening the aggregation by talc of Patent Document 1. Since talc contains magnesium which is a divalent metal salt, there is a problem that it cannot be applied to an active ingredient such as an antibiotic which can form a chelate with a metal salt. The method in the document has posed a problem that, when filling in a conical vessel is carried out after mixing, the variation of the active ingredient content increases since lactose, of which particle size is considerably different from that of an active ingredient, is separated and segregated (see Table 5 in Comparative Example 1 of the present application). Thus, there has been a need for an additive which does not cause chemical reaction with a metal salt, provides sufficient uniformity of an active ingredient during mixing, and less easily causes the segregation of the active ingredient and the other additives even when receiving a gravitational force and vibration during the steps of transport, input, filling, and the like.

Patent Document 3 describes a production method of a solid preparation characterized in that a composition containing a β-1,4glucan powder having an average particle size of at most 30 μm and a specific surface area of 1.3 m²/g or more is shaped by a dry granulation method or a dry granule compression method. This document describes that the separation and segregation of granules and ingredients added later are a problem, particularly in a production method of tablets called a wet granulation and tableting with extra-granular addition of disintegrant, which involves preparing in advance granules containing a principal agent and then compressing after adding a binder or a disintegrant and a lubricant. Thus, the problem of the document is equivalent to that of the wet granulation and tableting with extra-granular addition of disintegrant. However, because of high repose angle and low fluidity of β-1,4 glucan powders of the document, there has been a problem that, since the fluidity of the mixture becomes lower by adding β-1,4 glucan powders of the document having low fluidity to an active ingredient of which particle size is rendered small, the composition is not filled into a die, and even tableting is not possible, though it can exert its advantageous effect when used with particles having a large particle size and a certain level of fluidity, such as a granule containing a principal agent in advance (see Comparative Examples 18 and 19 in the present application). That is, the problem of separation and segregation in the direct compression has not been able to be solved. A 30-μm-or-less cellulose powder which has such a good repose angle as to be able to improve the fluidity of an active ingredient having a small average particle size and can suppress the separation and segregation of the active ingredient having a small average particle size has not been known.

Patent Document 4 describes a formulating agent for cosmetics which is a white fine powder of microcrystalline cellulose, has the ratio of a major to minor axis of the particle of 3 or less, predominantly takes the form of a near oval particle, is present as 30-μm-or-more particles in an amount of 0 to 10% by weight, and has an average particle size of 3 to 30 μm. This document describes that because the formulating agent has a particle size close to that of inorganic powders widely used in cosmetic applications, the separation and segregation of different powders due to the difference in the particle size are reduced. However, there has been a problem that, since the formulating agent for cosmetics in the document has too high a repose angle and low fluidity in comparison with an active ingredient of which average particle size is rendered small in pharmaceutical and health food applications, it cannot improve the fluidity so as to be tabletted (see Comparative Examples 20 and 21 in the present application). That is, the problem of separation and segregation in the direct compression in the field of pharmaceutical, health food, and the like has not been able to be solved. Thus, a cellulose powder for use in medicine, health and other applications which enables the tableting of an active ingredient of which average particle size is rendered small and can suppress separation and segregation has not been known.

Patent Document 5 describes a microcrystalline cellulose aggregate having an average polymerization degree of 60 to 375, an apparent specific volume of 1.6 to 3.1 cm³/g, an apparent tapping specific volume of 1.4 cm³/g or more, and a repose angle of 35 to 42°, and containing 2 to 80% by weight of a component of 200 meshes or more, as a cellulose powder excellent in fluidity and disintegration. Though Example 7 of the Patent Document discloses cellulose having an average particle size of 20 μm and a repose angle of 34° as Comparative Example of the Document, it describes that the cellulose had too high fluidity and actually raised separation during outflow from a hopper. This provides the findings that preparation of a cellulose powder having a small average particle size and good fluidity may not necessarily lead to the suppression of separation and segregation. Actually, the use of a microcrystalline cellulose aggregate of the Examples in which no separation or segregation occurred in the Patent Document cannot sufficiently suppress the separation and segregation of an active ingredient having a small average particle size although it has improved the fluidity of the active ingredient having a small average particle size (see Comparative Example 22 in the present application). Thus, this Patent Document neither describes nor suggests powder physical properties necessary to suppress the separation and segregation.

Patent Document 6 describes a core seed containing 50% by mass or more of crystalline cellulose and having an average particle size of greater than or equal to 50 μm and less than 100 μm, a relative fluidity index of 7.0 to 15.0, a specific surface area of less than 0.15 m²/g, and a tapping bulk density of 0.80 g/mL or more. This Patent Document describes a granule-containing tablet obtained by mixing and compressing coated granules, prepared by layering an active ingredient on core seeds, with additives such as a binder, a disintegrant and a lubricant. It also discloses that the content variation of the active ingredient in the tablet is small. However, as in Patent Document 3, there has been a problem that, though this method can exert an advantageous effect when used with granules containing an active ingredient having a large particle size and a certain level of fluidity, the separation and segregation of an active ingredient of which average particle size is rendered small cannot be sufficiently suppressed if the crystalline cellulose described in this document, "Ceolus"

KG-802 (equivalent to the cellulose powder of Patent Document 7), is used alone because the active ingredient itself has low fluidity (see Comparative Example 24 in the present application).

As described above, conventional techniques have had problems that it is difficult to form into a tablet with an active ingredient of which average particle size is rendered small because an additive having a small average particle size has a large repose angle, as shown in Patent Documents 3 and 4; that the separation and segregation of an active ingredient cannot be suppressed even if an additive having a small average particle size, a small repose angle and good fluidity is used, as shown in Patent Document 5; and that the separation and segregation of an active ingredient of which average size is rendered small cannot be sufficiently suppressed by just using the cellulose powder disclosed in Patent Document 2 or 7.

Means for Solving the Problems

As a result of investigating phenomena during mixing and during filling in a conical vessel simulating hopper filling before compression, the present inventors have found that, in order to suppress the segregation of an active ingredient and the other additives not only during mixing but also under a gravitational force and vibration during the steps of transport, input, filling, and the like after mixing, it is important to newly control the range of the internal frictional angle and adopt a specific particle structure in addition to controlling the average particle size, the repose angle, the bulk density, the tapping bulk density, and the specific surface area in certain ranges.

In the conical vessel within which the filling step is simulated, on the condition that angles are established toward both ends of the conical vessel with the center of the conical vessel defined as 0°, if an internal frictional angle of a cellulose powder is too large, the powder remains in the low angle side while an ingredient having a large particle size and good fluidity is separated to the high angle sides, i.e., to both ends of the conical vessel; and if an internal frictional angle of a cellulose powder is too small, the movement of an ingredient having a large particle size and good fluidity to the high angle sides cannot be suppressed.

In addition, the average particle size and particle structure of a cellulose powder has been found to be closely related to the internal frictional angle of the cellulose powder. That is, it has been determined that the β-1,4glucan powder of Patent Document 3 has a small average particle size and irregularities formed on the particle surface because it is prepared by pulverization, and it is susceptible to the constraints of the particle and has a larger internal frictional angle because its primary particle is in bar axis form; and that the formulating agent for cosmetics of Patent Document 4 predominantly takes the form of a near oval particle and has a smaller internal frictional angle in addition to having a small average particle size because the particle has small irregularities on the surface and is less easily constrained. The internal frictional angle was also found to be not related to the fluidity (i.e., repose angle) of a powder. That is, the cellulose powder of Patent Document 3 has a large internal frictional angle and a high repose angle, while the cellulose powder of Patent Document 4 has a small internal frictional angle and a high repose angle. It is not the internal frictional angle but the particle size and particle structure of a powder that affect the repose angle. The powder having a small particle size and present as a primary particle has a higher repose angle. To control the repose angle to the low side, it is found to be necessary to form a secondary aggregation structure in which primary particles are aggregated.

Specifically, the present invention is as follows:

(1) A cellulose powder comprising a cellulose type I crystalline and having an average particle size of less than 30 μm, a bulk density of 0.1 to 0.45 g/cm$^3$, a tapping density of 0.1 to 0.5 g/cm$^3$, a repose angle of 35 to 50°, a specific surface area of greater than or equal to 0.1 and less than 20 m$^2$/g and an internal frictional angle of 36 to 42°.

(2) The cellulose powder according to item (1), wherein the cellulose powder comprises particles having a secondary aggregation structure formed by aggregation of primary particles.

(3) The cellulose powder according to item (2), wherein the cellulose powder comprises 10 to 100% by weight of the particles having a secondary aggregation structure formed by aggregation of primary particles.

(4) A composition comprising one or more active ingredients and the cellulose powder according to any one of items (1) to (3).

(5) The composition according to item (4), wherein the active ingredient is an active ingredient for pharmaceuticals.

(6) The composition according to item (4), wherein the active ingredient is an active ingredient for health food.

(7) The composition according to item (5) or (6), wherein the active ingredient for pharmaceuticals or the active ingredient for health food is an ingredient which chemically reacts with a metal salt.

(8) A method for producing a molded product, comprising directly compressing the composition according to any one of items (4) to (7).

(9) A method for producing the cellulose powder according to items (1) to (3), comprising the steps of: obtaining an aqueous dispersion in which an average particle size of a natural cellulosic material is 1 to 20 μm and a solid content concentration is 20% by weight or less; and spray-drying the dispersion at a rotator speed of 40 to 200 m/sec.

(10) The method for producing a cellulose powder according to item (9), wherein the natural cellulosic material is one obtained by hydrolyzing pulp fibers having an average thickness of 0.5 to 5 μm.

Advantages of the Invention

The cellulose powder of the present invention is superior in prevention of the separation and segregation of an active ingredient in a composition containing the active ingredient in the pharmaceutical, health food, food and industrial fields. Therefore, using the cellulose powder of the present invention as an agent for preventing segregation in the production of a composition containing an active ingredient makes it possible to improve the content uniformity of the active ingredient which is hardly uniformly dispersed and further to suppress the occurrence of the segregation of the active ingredient and the other additives even under a gravitational force and vibration during the steps of transport, input, filling and the like after mixing.

BEST MODE FOR CARRYING OUT THE INVENTION

Figure 1:
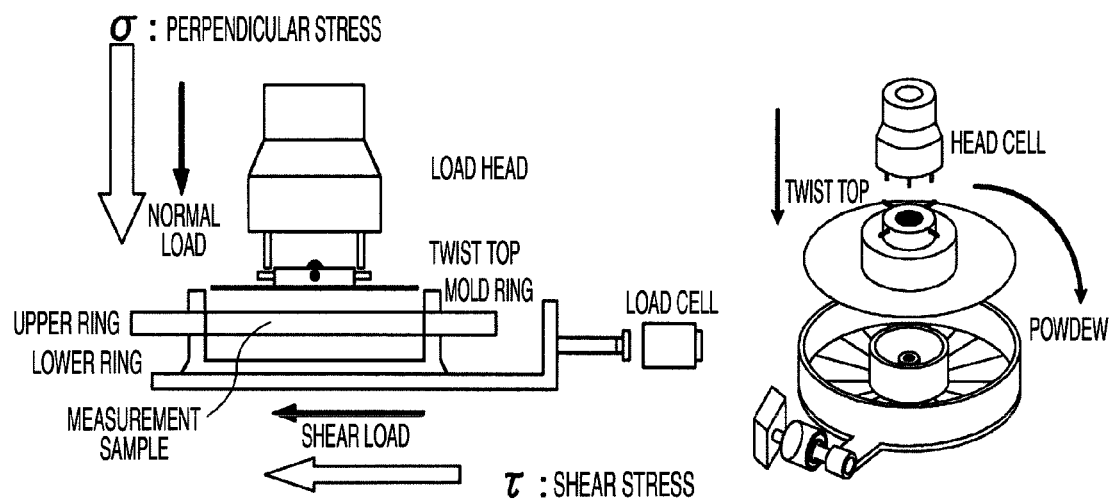
FIG. 1 is a drawing (upper) showing application of perpendicular stress (a) and shear stress (t) with ShearScan TS12 (Nihon Rufuto Co., Ltd. (trade name)) and a drawing (lower) showing an yield locus.
Figure 1:
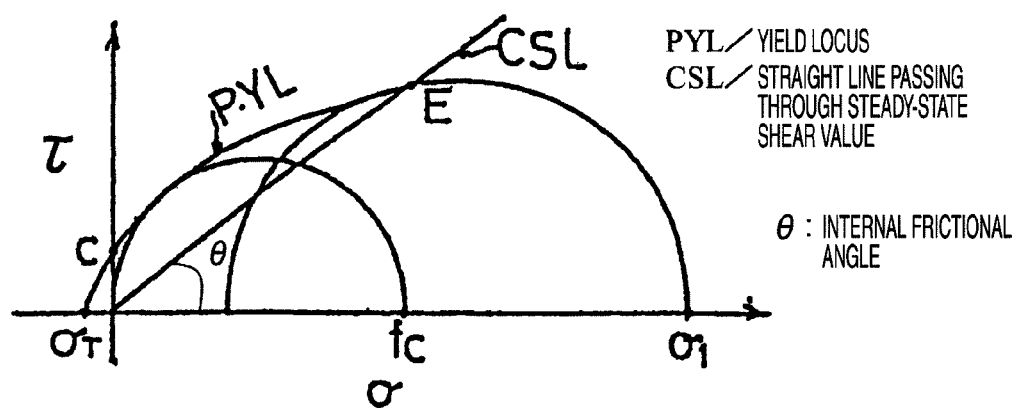

The present invention will be specifically described below, particularly with a focus on preferred embodiments thereof.

As used herein, the active ingredient is one which has the effect of preventing the separation and segregation of an active ingredient and the other additives in a composition in the pharmaceutical, health food, food and industrial fields.

The cellulose powder of the present invention needs to be a type I crystalline. Type I, type II, type III, and type IV are known as a crystal form of cellulose. Type I is excellent in terms of cost/environmental impact since it has the same crystal structure as native celluloses such as ramie, cotton linter and wood pulp, and thus, it only requires a natural resource without special treatment.

The cellulose powder of the present invention needs to have an average particle size of less than 30 μm. A particle size of 30 μm or more is undesirable because it allows the particles to be less easily dispersed in a composition containing an active ingredient and the other additives. The lower limit is, but not particularly limited to, at smallest about 1 μm. The average particle size is preferably 8 to 28 μm, more preferably 10 to 26 μm.

The cellulose powder of the present invention needs to have a bulk density of 0.1 to 0.45 g/cm$^3$ and a tapping bulk density of 0.1 to 0.5 g/cm$^3$. If a bulk density is more than 0.45 g/cm$^3$ or a tapping density is more than 0.5 g/cm$^3$, the segregation due to the density difference from an active ingredient and the other additives easily occurs. If it is less than 0.1 g/cm$^3$, the mixing efficiency is reduced and the handling property is lowered.

The cellulose powder of the present invention needs to have a repose angle of 35 to 50°. A repose angle of less than 35° is undesirable because it is liable to cause the segregation of an active ingredient. The segregation is attributed to the density difference and the after-mentioned internal frictional angle. A repose angle of more than 50° is undesirable because it makes low the fluidity of a composition containing an active ingredient. Preferred is 36 to 50°, particularly preferred 38 to 50°.

The cellulose powder of the present invention needs to have a specific surface area of greater than or equal to 0.1 and less than 20 m$^2$/g. A specific surface area of 20 m$^2$/g or more is undesirable since it strengthens its interaction with an active ingredient and poses problems of coloration and the like. The lower limit is at least about 0.1 m$^2$/g.

The cellulose powder of the present invention also needs to have an internal frictional angle of 35 to 42°. If it is less than 35°, the separation and segregation from the other ingredients easily occur since the friction of the particle surface becomes too small. If it is more than 42°, the friction of the particle surface becomes too large for the cellulose powder to be sufficiently dispersed in a composition to contribute to making an active ingredient and the other ingredients uniform. Preferred is 36 to 42°, particularly preferred 36 to 41°. Even when the active ingredient has an average particle size different from those of other additives, the internal frictional angle being in the scope of the present invention can prevent the separation and segregation and impart appropriate fluidity because the fluidities of the respective particles can be adjusted by the cellulose powder of the present invention penetrated between the respective particles.

The cellulose powder of the present invention preferably comprises a secondary aggregation structure formed by aggregation of primary particles. As used herein, the secondary aggregation structure refers to a particle composed of a plurality of primary particles when the particle is observed at 200 to 1000-fold magnification by a scanning electron microscope (SEM). The cellulose powder having the secondary aggregation structure formed by aggregation of primary particles dramatically improves fluidity (repose angle) in comparison with that only consisting of primary particles. In addition, the surface smoothness of the secondary aggregated particles and the percentage of the secondary aggregated particles greatly affect the magnitude of the internal frictional angle. It cannot necessarily be determined to what extent the secondary aggregated particles need to be blended because it also depends on the surface smoothness of the secondary aggregated particles. When a percentage of secondary aggregated particles is 10% or less of the total, an internal frictional angle tends to be more than 42°. The more secondary aggregated particles are preferable. The surface smoothness of the secondary aggregated particles is affected by the degree of intensity of the attrition received by cellulose primary particles. The degree of attrition can be intensified to increase the surface smoothness by treatment such as hydrolysis to the level-off polymerization degree or grinding the slurry. The degree of intensity of attrition can be properly adjusted by measuring the average particle size of cellulose primary particles in the slurry. A smaller average particle size of the cellulose primary particles tends to result in a higher degree of intensity of attrition although it is not necessarily decided because the degree of intensity of attrition varies depending on the stirring speed during hydrolysis and the degree and frequency of grinding.

The percentage of the secondary aggregated particles can be properly adjusted by controlling the slurry concentration during spray drying. A lower slurry concentration decreases the percentage of the secondary aggregated particles, and a higher slurry concentration increases the percentage of the secondary aggregated particles.

In contrast, a higher slurry concentration tends to increase the average particle size of the cellulose particles after drying. For spray drying with a rotator, increasing the rotator speed can decrease the size of droplets.

It has conventionally been believed that the average particle size of cellulose particles after drying is enlarged when the percentage of secondary aggregated particles is increased, and is hardly controlled to be less than 30 μm. Thus, it has conventionally been thought that cellulose particles not only having an average size of less than 30 μm but also comprising secondary aggregated particles cannot be obtained. However, the present inventors have found that they can be obtained by applying a specific cellulose concentration and a specific rotator speed to a drying method using spray drying.

In a die, 0.5 g of the cellulose powder of the present invention is placed and compressed at a stress of 10 MPa by a flat punch 1.13 cm in diameter with the stress held for 10 seconds to provide a cylindrical molded product (PCM-1A from Aikoh Engineering Co. Ltd. was used for the compression and the compression speed was about 10 cm/min.). The cylindrical molded product is loaded along the diametrical direction of the cylindrical molded product using Shleuniger hardness tester (Model 6D from Freund Industrial Co., Ltd.) for breakage. The load at breakage is preferably in the range of 20 to 50 N. An internal frictional angle of less than 36° tends to result in a breaking load of less than 20 N, and more than 42°, in a breaking load of more than 50 N.

The method for producing the cellulose powder of the present invention will be described below.

The cellulose powder of the present invention is, for example, obtained by comprising the steps of obtaining an aqueous dispersion having an average particle size of cellulose of 1 to 20 μm and a solid content concentration of 1 to 20% by weight when the cellulose was dispersed, and spray-drying the dispersion at a rotator speed of 40 to 200 m/sec.

The cellulose powder of the present invention comprises a natural cellulosic material. The natural cellulosic material may be of plant or animal origin, is a fibrous material derived from a natural product containing a cellulose such as wood, bamboo, wheat straw, rice straw, cotton, ramie, bagasse, kenaf, beet, hoya, or bacterial cellulose, and needs to have a cellulose type I crystalline structure. As a raw material, one natural cellulosic material of the above described materials may be used, or a mixture of two or more thereof can be used. These are preferably used in the form of purified pulps. A method for purifying pulps is not particularly limited; any pulp including dissolving pulp, kraft pulp, or NBKP pulp may be used. Here, the natural cellulosic material may be one obtained by hydrolyzing or unhydrolyzing a raw material such as a pulp. For hydrolysing, acid hydrolysis, alkali oxidative decomposition, hydrothermal decomposition, steam explosion, or the like may be used. These methods may be used alone, or two or more of them may be combined. Pulp fibers having an average width of 2 to 30 μm and an average thickness of 0.5 to 5 μm are preferably used because the cellulose particles become easily entangled owing to the small average thickness and tend to form secondary aggregated particles.

In the above production method, the medium used when the solid content containing a natural cellulosic material is dispersed in an appropriate medium is preferably water, but is not particularly limited provided that it is industrially used. For example, water and/or an organic solvent may be used. Examples of the organic solvent include alcohols such as methanol, ethanol, isopropyl alcohol, butyl alcohol, 2-methylbutyl alcohol, and benzyl alcohol; hydrocarbons such as pentane, hexane, heptane, and cyclohexane; and ketones such as acetone and ethyl methyl ketone. Particularly, the organic solvent is preferably one used in pharmaceutical preparations. Examples thereof include those classified as solvent in "Japanese Pharmaceutical Excipients Directory" (issued by Yakuji Nippo Limited). Water and organic solvents may be used alone, or two or more of them may be combined. After dispersing in one type of medium and removing the medium, the dispersion may be carried out with a different medium.

The cellulose dispersion particles preferably have an average particle size of 1 to 20 μm. More preferred is 3 to 20 μm, particularly preferably 7 to 18 μm. An average particle size of 20 μm or more results in an average size of the dried cellulose particles of more than 30 μm and is undesirable because it causes the particles to be less easily dispersed in a composition. Depending on the degree of grinding, the lower limit is at least about 1 μm. As used herein, the average particle size is a particle size at a cumulative volume of 50% measured by a laser diffraction particle size distribution analyzer (Model LA-910 (trade name) from Horiba).

The average particle size of the cellulose dispersion particles can be controlled in a desired range by adjusting the polymerization degree of a raw material cellulose by hydrolysis and the stirring force during the step of hydrolysis and/or dispersion of the cellulose. An increase in the acid or alkali concentration or the reaction temperature of the hydrolyzed solution generally tends to result in a reduction in the cellulose polymerization degree and a decrease in the average cellulose particle size in the dispersion. An increase in the stirring force to the solution also tends to result in a decrease in the average particle size of the cellulose dispersion particles. For example, the average particle size of the cellulose dispersion particles can be adjusted to 20 μm or less by hydrolyzing pulp fibers having an average width of 2 to 30 μm and an average thickness of 0.5 to 5 μm at 100 to 140° C. with 0.1 to 10% hydrochloric acid under increased pressure and subsequently setting the product of the stirring blade diameter (m) and the number of stirring revolutions (rpm) to 10 to 200. As an alternative method, it can be obtained by grinding the cellulose dispersion. As a grinding method, a method using a stirring blade such as one-direction rotation type, multi-axis rotation type, reciprocal inversion type, vertical movement type, rotation+vertical movement type, and piping type such as a portable mixer, a three-dimensional mixer, and a sidewall mixer; a jet type stirring grinding method such as a line mixer; a grinding method using a high shear homogenizer, a high pressure homogenizer, a supersonic wave homogenizer, or the like; or a grinding method of an axial rotation extrusion type such as a kneader, may be used. As a pulverizing method, any of a screen-type pulverizing method such as a screen mill and a hammer mill, a blade rotation shear screen type pulverizing method such as a flush mill, an air stream type pulverizing method such as a jet mill, a ball type pulverizing method such as a ball mill and a vibratory ball mill, and a blade stirring type pulverizing method. However, overgrinding is undesirable because the bulk density and the internal frictional angle are beyond the specific ranges. If, though it depends on the extent of grinding, the percentage of particles having a particle size of 10 μm or more decreases to less than 20% based on the total, the bulk density is heavy and the internal frictional angle is too small. If the percentage increases to more than 90% based on the total, the average particle size of the dried particles cannot be less than 30 μm. For example, kneading in a versatile mixer for 10 minutes or more is undesirable because the percentage of particles having a particle size of 10 μm or more decreases to less than 20% although the average particle size is comparable, and the bulk density exceeds the upper limit of the present invention. In order for the dried cellulose powder to satisfy both ranges of the bulk density and internal frictional angle of the present invention, the percentage of cellulose particles having a particle size of 10 μm or more is particularly preferably 20 to 90% with the cellulose dispersion particles having an average particle size of about 7 to 18 μm.

The cellulose dispersion obtained by the above operation preferably has a solid content concentration of 1 to 20% by weight. More than 20% by weight is undesirable because it makes the average particle size of the resulting cellulose particles too large even at a specific range of rotator speed and causes the repose angle and the internal frictional angle to be beyond the specific ranges, resulting in impairment of the effect of preventing separation and segregation may be used. Less than 1% by weight is undesirable because secondary aggregated particles are less easily formed.

For example, any of lyophilization, spray drying, drum drying, shelf drying, air stream drying and vacuum drying may be used, but is not particularly limited to, as a drying method. These methods may be used alone, or two or more of them may be combined. When spray drying is performed, any spray drying method, such as a disc type, a pressure nozzle type, a compressed two-fluid nozzle type and a compressed four-fluid nozzle type may be used as the spraying method. These methods may be used alone, or two or more of them may be combined. When the spray drying is performed, a very small amount of a water-soluble polymer or a surfactant may be added for the purpose of lowering the surface tension of the dispersion, or a blowing agent or gas may be added to the dispersion for the purpose of promoting the vaporization rate of the medium. To render the average particle size of the dried cellulose small, a method in which the speed of a disc type rotator is increased is most efficient. For example, the average particle size can be rendered less than 30 μm by spray drying in the range of 40 to 200 m/sec.

As used herein, the active ingredient refers to a substance added to exert its function and effect intended in the pharmaceutical, health food, food, industrial and other fields in a powder mixture, a molded product, a processed product, or the like. For example, the active ingredient in the pharmaceutical field is a pharmaceutical medicinal ingredient.

The blending percentage of the cellulose powder of the present invention is preferably about 0.1 to 50% by weight. More preferred is 0.1 to 20% by weight, particularly preferred 0.1 to 10% by weight.

As an active ingredient for a medicament, a substance which can be orally administered, such as antipyretic analgesic anti-inflammatory, sedative hypnotic, drowsiness preventing, dizziness suppressing, children's analgesic, stomachic, antacid, digestive, cardiotonic, antiarrhythmic, hypotensive, vasodilator, diuretic, antiulcer, intestinal function-controlling, bone-building, antitussive expectorant, antiasthmatic, antimicrobial, pollakiuria-improving, analeptic drugs, and vitamins, can be a target of the present invention. The medicinal ingredient may be used alone, or two or more of them may be combined. Specific examples thereof can include pharmaceutical medicinal ingredients as described in "Japanese Pharmacopeia", "JPC", "USP", "NF", or "EP", including aspirin, aspirin aluminium, acetaminophen, ethenzamide, sasapyrine, salicylamide, lactylphenetidin, isotibenzyl hydrochloride, diphenylpyraline hydrochloride, diphenhydramine hydrochloride, difeterol hydrochloride, triprolidine hydrochloride, tripelenamine hydrochloride, thonzylamine hydrochloride, fenethazine hydrochloride, methdilazine hydrochloride, diphenhydramine salicylate, carbinoxamine diphenyldisulfonate, alimemazine tartrate, diphenhydramine tannate, diphenylpyraline chlorotheophyllinate, mebhydrolin napadisylate, promethazine methylenedisalicylate, carbinoxamine maleate, chlorpheniramine dl-maleate, chlorpheniramine d-maleate, difeterol phosphate, alloclamide hydrochloride, cloperastine hydrochloride, pentoxyverine citrate (carbetapentane citrate), tipepidine citrate, dibunate sodium, dextromethorphan hydrobromide, dextromethorphan-phenolphthalic acid, tipepidine hibenzate, chloperastine fendizoate, codeine phosphate, dihydrocodeine phosphate, noscapine hydrochloride, noscapine, dl-methylephedrine hydrochloride, dl-methylephedrine saccharin salt, potassium guaiacolsulfonate, guaifenesin, caffeine and sodium benzoate, caffeine, anhydrous caffeine, vitamin B1 and its derivatives and their salts, vitamin B2 and its derivatives and their salts, vitamin C and its derivatives and their salts, hesperidin and its derivatives and their salts, vitamin B6 and its derivatives and their salts, nicotinic acid amide, calcium pantothenate, aminoacetic acid, magnesium silicate, synthetic aluminum silicate, synthetic hydrotalcite, magnesia oxide, dihydroxyaluminum-aminoacetate (aluminum glycinate), aluminium hydroxide gel (as dried aluminium hydroxide gel), dried aluminium hydroxide gel, aluminium hydroxide-magnesium carbonate mixed dried gel, aluminium hydroxide-sodium hydrogen carbonate coprecipitation product, aluminium hydroxide-calcium carbonate-magnesium carbonate coprecipitation product, magnesium hydroxide-potassium aluminum sulfate coprecipitation product, magnesium carbonate, magnesium aluminometasilicate, ranitidine hydrochloride, cimetidine, famotidine, naproxen, diclofenac sodium, piroxicam, azulene, indometacin, ketoprofen, ibuprofen, difenidol hydrochloride, diphenylpyraline hydrochloride, diphenhydramine hydrochloride, promethazine hydrochloride, meclizine hydrochloride, dimenhydrinate, diphenhydramine tannate, fenethazine tannate, diphenylpyraline chlorotheophyllinate, diphenhydramine fumarate, prometthazine methylenedisalicylate, scopolamine hydrobromide, oxyphencyclimine hydrochloride, dicyclomine hydrochloride, methixene hydrochloride, atropine methylbromide, anisotropine methylbromide, scopolamine methylbromide, methyl-1-hyoscyamine bromide, methylbenactyzium bromide, belladonna extract, isopropamide iodide, diphenylpiperidinomethyldioxolan iodide, papaverine hydrochloride, aminobenzoic acid, cesium oxalate, ethyl piperidinoacetylaminobenzoate, aminophyllin, diprophylline, theophylline, sodium hydrogen carbonate, fursultiamine, isosorbide nitrate, ephedrine, cefalexin, ampicillin, sulfixazole, sucralfate, allyl isopropylacetyl urea, bromovalerylurea and the like, ephedra herb, Nandina fruit, yellow bark, polygala root, licorice, platycodon root, plantago seed, plantago herb, senega root, fritillaria bulb, fennel, phellodendron bark, coptis rhizome, zedoary, matricaria, cassia bark, gentian, oriental bezoar, beast gall (containing bear bile), adenophorae radix, ginger, atractylodes lancea rhizome, clove, citrus unshiu peel, atractylodes rhizome, earthworm, panax rhizome, ginseng, japanese valerian, moutan bark, zanthoxylum fruit and their extracts, insulin, vasopressin, interferon, urokinase, serratio peptidase, and somatostatin; one selected from the above may be used, or two or more of them may be combined.

The ingredient for health food is not limited provided that it is an ingredient blended for the purpose of augmenting health. For example, it includes powdered green juice, aglycone, agaricus, ashwagandha, astaxanthin, acerola, amino acids (valine, leucine, isoleucine, lysine, methionine, phenylalanine, threonine, tryptophan, histidine, cystine, tyrosine, arginine, alanine, aspartic acid, powdered seaweed, glutamine, glutamic acid, glycin, proline, serine, etc.), alginic acid, ginkgo biloba extract, sardine peptides, turmeric, uronic acid, echinacea, Siberian ginseng, oligosaccharides, oleic acid, nucleoproteins, dried skipjack peptides, catechin, potassium, calcium, carotenoid, garcinia cambogia, L-carnitine, chitosan, conjugated linoleic acid, Aloe arborescens, Gymnema sylvestre extract, citric acid, Orthosiphon stamineus, glycerides, glycenol, glucagon, curcumin, glucosamine, L-glutamine, chlorella, cranberry extract, Uncaria tomentosa, germanium, enzymes, Korean ginseng extract, coenzyme Q10, collagen, collagen peptides, coleus blumei, chondroitin, powdered psyllium husks, Crataegi fructus extract, saponin, lipids, L-cystine, Japanese basil extract, citrimax, fatty acids, phytosterol, seed extract, spirulina, squalene, Salix alba, ceramide, selenium, St. John's wort extract, soy isoflavone, soy saponin, soy peptides, soy lecithin, monosaccharides, proteins, chaste tree extract, iron, copper, docosahexaenoic acid, tocotrienol, nattokinase, Bacillus natto culture extract, sodium niacin, nicotine acid, disaccharides, lactic acid bacterium, garlic, saw palmetto, sprouted rice, pearl barley extract, herb extract, valerian extract, pantothenic acid, hyaluronic acid, biotin, chromium picolinate, vitamin A and A2, vitamin B1, B2 and B6, vitamin B12, vitamin C, vitamin D, vitamin E, vitamin K, hydroxytyrosol, bifidobacterium, beer yeast, fructo oligosaccharides, flavonoid, Butcher's broom extract, black cohosh, blueberry, prune concentrate, proanthocyanidin, proteins, propolis, bromelain, probiotics, phosphatidylcholine, phosphatidylserine, β-carotene, peptides, safflower extract, Grifola frondosa extract, maca extract, magnesium, milk thisthle, manganese, mitochondria, mineral, mucopolysaccharides, melatonin, Fomes yucatensis, powdered melilot extract, molybdenum, vegetable powder, folic acid, lactose, lycopene, linolic acid, lipoic acid, phosphorus, lutein, lecithin, rosmarinic acid, royal jelly, DHA, and EPA.

The active ingredient may be poorly-soluble or soluble in water. The term "poorly-soluble" refers to 30 mL or more of water being required to dissolve 1 g of a solute in the Japanese Pharmacopoeia Fourteenth Edition. Examples of the solid active ingredient poorly-soluble in water can include pharmaceutical medicinal ingredients as described in "Japanese Pharmacopeia", "JPC", "USP", "NF", or "EP", including antipyretic analgesics, drugs for the nervous system, hypnotics and sedatives, muscle relaxants, blood pressure hardeners, antihistamines, and the like such as acetaminophen, ibuprofen, benzoic acid, ethenzamide, caffeine, camphor, quinine, calcium gluconate, dimercaprol, sulfamine, theophylline, theobromine, riboflavin, mephenesin, phenobarbital, aminophyllin, thioacetazone, quercetin, rutin, salicylic acid, theophylline sodium salt, pyrapital, quinine hydrochloride, irgapyrin, dikitoxin, griseofulvin, and phenacetin; antibiotics such as acetylspiramycin, ampicillin, erythromycin, kisatamycin, chloramphenicol, triacetyloleandomycin, nystatin, and colistin sulfate; steroid hormones such as methyltestosterone, methylandrostetronediol, progesterone, estradiol bezoate, ethynyl estradiol, deoxycorticosterone acetate, cortisone acetate, hydrocortisone, hydrocortisone acetate, and brednisolone; non-steroidal yolk hormone drugs such as dienestrol, hexastrol, diethylstilbestrol, diethylstilbesterol dibrohionate, and chlorotrianisene. One selected from the above may be used, or two or more of them may be combined. When the active ingredient is poorly soluble in water, it can exhibit an effect irrespective of the degree of sublimation and surface polarity by being blended in the composition of the present invention.

The active ingredient may be a poorly water-soluble oily or liquid form. Examples of the poorly water-soluble oily or liquid active ingredient include pharmaceutical medicinal ingredients as described in "Japanese Pharmacopeia", "JPC", "USP", "NF", or "EP", including vitamins such as teprenone, indomethacin farnesyl, menatetrenone, phytonadione, vitamin A oil, fenipentol, vitamin D, and vitamin E; higher unsaturated fatty acids such as DHA (docosahexaenoic acid), EPA (eicosapentaenoic acid), and liver oil; coenzyme Qs; and oil-soluble flavorings such as orange, lemon, and peppermint oils. For vitamin E, there are various homologues and derivatives thereof, which are used in the present invention without particular restriction if they are in liquid form at ordinary temperature. These can include, for example, dl-α-tocopherol, dl-α-tocopherol acetate, d-α-tocopherol, and d-α-tocopherol acetate; one selected from the above may be used, or two or more thereof may be used in combination.

The active ingredient may be a poorly water-soluble semi-solid active ingredient. Examples of the poorly water-soluble semi-solid active ingredient can include Chinese herbal medicines or crude drug extracts such as earthworm, licorice, cassia bark, peony root, moutan bark, japanese valerian, zanthoxylum fruit, ginger, citrus unshiu peel, ephedra herb, nandina fruit, yellow bark, polygala root, platycodon root, plantago seed, plantago herb, shorttube lycoris, senega root, fritillaria bulb, fennel, phellodendron bark, coptis rhizome, zedoary, matricaria, gentian, oriental bezoar, beast gall, adenophorae radix, ginger, atractylodes lancea rhizome, clove, citrus unshiu peel, atractylodes rhizome, panax rhizome, ginseng, kakkonto, keihito, kousosan, saiko-keishito, shosaikoto, shoseiryuto, bakumondoto, hangekobokuto, and maoto, an oyster meat essence, propolis or an extract thereof, and coenzyme Qs; one selected from the above may be used, or two or more of them may be combined. The solid preparation composition of the present invention may further contain other physiologically active ingredients in addition to the above poorly water-soluble active ingredient.

The finely ground active ingredient used in the present invention may be one finely ground to 1 to 40 µm or less, for the purpose of, for example, improving the dispersibility of the poorly water-soluble solid active ingredient or improving the mixing uniformity of the active ingredient having efficacy in a very small amount. A smaller average particle size of the active ingredient increases the advantages of the present invention. The average particle size of the active ingredient is more preferably 1 to 20 µm and still more preferably 1 to 10 µm.

As used herein, the sublimation ingredient in active ingredients is not particularly limited provided that it has sublimation. It may be any state of solid, liquid or semi-solid at ordinary temperature.

The active ingredient may be a sublimation one. Examples of the sublimation active ingredient include sublimation pharmaceutical medicinal ingredients as described in "Japanese Pharmacopeia", "JPC", "USP", "NF", or "EP", including benzoic acid, ethenzamide, caffeine, camphor, salicylic acid, phenacetin, and ibuprofen; one selected from the above may be used, or two or more of them may be combined. The solid preparation composition of the present invention may further contain other physiologically active ingredients in addition to the above sublimation active ingredient.

"Other additives" as used herein may include an excipient, a disintegrant, a binder fluidizing agent, a lubricant, and a corrigent. Examples of the excipient include ones classified as an excipient in "Japanese Pharmaceutical Excipients Directory" (issued by Yakuji Nippo Limited), including acrylated starch, L-asparagic acid, aminoethyl sulfonic acid, aminoacetate, wheat gluten (powder), gum arabic, powdered acacia, alginic acid, sodium alginate, pregelatinized starch, light gravel granule, inositol, ethyl cellulose, ethylene-vinyl acetate copolymer, sodium chloride, olive oil, kaolin, cacao butter, casein, fructose, light gravel granule, carmellose, carmellose sodium, silicon dioxide hydrate, dry yeast, dried aluminum hydroxide gel, dried sodium sulfate, dried magnesium sulfate, agar, agar powder, xylitol, citric acid, sodium citrate, disodium citrate, glycerin, calcium glycerophosphate, sodium gluconate, L-glutamine, clay, clay 3, clay grain, croscarmellose sodium, crospovidone, magnesium aluminosilicate, calcium silicate, magnesium silicate, light silicic anhydride, light liquid paraffin, cinnamon powder, crystalline cellulose, crystalline cellulose-carmellose sodium, crystalline cellulose (grain), brown rice malt, synthetic aluminum silicate, synthetic hydrotalcite, sesame oil, wheat flour, wheat starch, wheat germ powder, rice powder, rice starch, potassium acetate, calcium acetate, cellulose acetate phthalate, safflower oil, white beeswax, zinc oxide, titanium oxide, magnesium oxide, β-cyclodextrin, dihydroxyaluminum aminoacetate, 2,6-dibutyl-4-methylphenol, dimethylpolysiloxane, tartaric acid, potassium hydrogen tartrate, plaster, sucrose fatty acid ester, alumina magnesium hydroxide, aluminum hydroxide gel, aluminum hydroxide/sodium hydrogen carbonate coprecipitate, magnesium hydroxide, squalane, stearyl alcohol, stearic acid, calcium stearate, polyoxyl stearate, magnesium stearate, soybean hardened oil, purified gelatine, purified shellac, purified sucrose, purified sucrose spherical granulated powder, cetostearyl alcohol, polyethylene glycol 1000 monocetyl ether, gelatine, sorbitan fatty acid ester, D-sorbitol, tricalcium phosphate, soybean oil, unsaponified soy bean, soy bean lecithin, powdered skim milk, talc, ammonium carbonate, calcium carbonate, magnesium carbonate, neutral anhydrous sodium sulfate, low substitution degree hydroxypropylcellulose, dextran, dextrin, natural aluminum silicate, corn starch, powdered tragacanth, silicon dioxide, calcium lactate, lactose, lactose granulated substance, par filler 101, white shellac, white vaseline, white clay, sucrose, sucrose/starch spherical granulated powder, naked barley green leaf extract, dried powder of bud and leaf juice of naked barley, honey, paraffin, potato starch, semi-digested starch, human serum albumin, hydroxypropyl starch, hydroxypropylcellulose, hydroxypropylcellulose, hydroxypropyl methylcellulose phthalate, hydroxypropyl methylcellulose phthalate, phytic acid, glucose, glucose hydrate, partially pregelatinized starch, pullulan, propylene glycol, starch syrup of reduced malt sugar powder, powdered cellulose, pectin, bentonite, sodium polyacrylate, polyoxyethylene alkyl ethers, polyoxyethylene hydrogenated castor oil, polyoxyethylene (105) polyoxypropylene (5) glycol, polyoxyethylene (160) polyoxypropylene (30) glycol, sodium polystyrene sulfonate, polysorbate 80, polyvinylacetal diethylamino acetate, polyvinylpyrrolidone, polyethylene glycol, maltitol, maltose, D-mannitol, water candy, isopropyl myristate, anhydrous lactose, anhydrous calcium hydrogenphosphate, anhydrous calcium phosphate granulated substance, magnesium aluminometasilicate, methyl cellulose, cottonseed powder, cotton oil, haze wax, aluminum monostearate, glyceryl monostearate, sorbitan monostearate, pharmaceutical carbon, peanut oil, aluminum sulfate, calcium sulfate, granular corn starch, liquid paraffin, dl-malic acid, calcium monohydrogen phosphate, calcium hydrogenphosphate, calcium hydrogenphosphate granulated substance, sodium hydrogenphosphate, potassium dihydrogen phosphate, calcium dihydrogen phosphate, and sodium dihydrogenphosphate; these may be used alone, or two or more of them may be combined.

Examples of the disintegrant can include ones classified as disintegrants in "Japanese Pharmaceutical Excipients Directory" (issued by Yakuji Nippo Limited), including croscarmellose sodium, carmellose, carmellose calcium, carmellose sodium, celluloses such as low substitution degree hydroxypropylcellulose, starches such as sodium carboxymethyl starch, hydroxypropyl starch, rice starch, wheat starch, corn starch, potato starch, and partly pregelatinized starch, and synthetic polymers such as crospovidone and crospovidone copolymer. One selected from the above may be used, or two or more thereof may be used.

Examples of the binder can include ones classified as binders in "Japanese Pharmaceutical Excipients Directory" (issued by Yakuji Nippo Limited), including saccharides such as sucrose, glucose, lactose and fructose, sugar alcohols such as mannitol, xylitol, maltitol, erythritol, and sorbitol, water-soluble polysaccharides such as gelatine, pullulan, carrageenan, locust bean gum, agar, glucomannan, xanthan gum, tamarind gum, pectin, sodium alginate, and Arabia gum, celluloses such as crystalline cellulose, powdered cellulose, hydroxypropylcellulose and methyl cellulose, starches such as pregelatinized starch and starch paste, synthetic polymers such as polyvinylpyrrolidone, carboxyvinyl polymer and polyvinyl alcohol, and inorganic compounds such as calcium hydrogenphosphate, calcium carbonate, synthetic hydrotalcite, and magnesium aluminosilicate. One selected from the above may be used, or two or more of them may be combined.

Examples of the fluidizing agent include ones classified as fluidizing agents in "Japanese Pharmaceutical Excipients Directory" (issued by Yakuji Nippo Limited), including silicon compounds such as silicon dioxide hydrate, and light silicic anhydride. One selected from the above may be used, or two or more of them may be combined.

Examples of the lubricant can include ones classified as lubricants in "Japanese Pharmaceutical Excipients Directory" (issued by Yakuji Nippo Limited), including magnesium stearate, calcium stearate, stearic acid, sucrose fatty acid ester, and talc. One selected from the above may be used, or two or more of them may be combined.

Examples of the corrigent can include ones classified as corrigents in "Japanese Pharmaceutical Excipients Directory" (issued by Yakuji Nippo Limited), including glutamic acid, fumaric acid, succinic acid, citric acid, sodium citrate, tartaric acid, malic acid, ascorbic acid, sodium chloride, and 1-menthol. One selected from the above may be used, or two or more of them may be combined.

Examples of the flavoring agent can include ones classified as flavoring agents in "Japanese Pharmaceutical Excipients Directory" (issued by Yakuji Nippo Limited), including orange, vanilla, strawberry, yogurt, menthol, oils such as fennel oil, cinnamon bark oil, orange peel oil, and peppermint oil, and green tea powder. One selected from the above may be used, or two or more of them may be combined.

Examples of the coloring agent used can include ones classified as coloring agents in "Japanese Pharmaceutical Excipients Directory" (issued by Yakuji Nippo Limited), including edible dyes such as edible red 3, edible yellow 5 and edible blue 1, sodium copper chlorophyllin, titanium oxide, and riboflavin. One selected from the above may be used, or two or more of them may be combined.

Examples of the sweetener used can include ones classified as sweeteners in "Japanese Pharmaceutical Excipients Directory" (issued by Yakuji Nippo Limited), including aspartame, saccharin, dipotassium glycyrrhizinate, stevia, maltose, maltitol, starch syrup, and powdered sweet hydrangea leaf. One selected from the above may be used, or two or more of them may be combined.

The method for producing a tablet after mixing one or more active ingredients and the cellulose powder of the present invention will be described below. These methods are illustrative only, and the advantageous effects of the invention are not limited by these methods. As the method for producing a tablet, a method which involves mixing an active ingredient(s) with the cellulose powder of the present invention and then subjecting the mixture to compression molding can be applied. Here, other additives may be blended as needed in addition to the active ingredient(s). As other additives, for example, one or more selected from the above described ingredients such as an excipient, a disintegrant, a binder, a fluidizing agent, a lubricant, a corrigent, a flavoring agent, a coloring agent, a sweetener, and a solubility enhancing agent may be blended.

The order of addition of the ingredients is not particularly limited; i) a method involving collectively mixing an active ingredient, the cellulose powder of the present invention, and, if necessary, other additives and then subjecting the mixture to compression molding or ii) a method involving premixing an active ingredient and additives such as a fluidizing agent and/or a lubricant, mixing the cellulose powder of the present invention and, if necessary, other additives, and then subjecting the mixture to compression molding may be used. In view of simplicity of operation, method i) is preferable. A lubricant may also be added to the powder mixture for compression molding obtained in method i) or method ii), which is further mixed and then subjected to compression molding.

A method for adding ingredients is not particularly limited provided that it is a commonly used method; they may be continuously added or collectively charged using a small size suction transport apparatus, an air transport apparatus, a bucket conveyor, a pneumatic transport apparatus, a vacuum conveyer, a vibration type quantitative metering feeder, a spray, a funnel and the like. As a spraying method, a method involving spraying an active ingredient solution/dispersion using a pressure nozzle, a two-fluid nozzle, a four-fluid nozzle, a turning disc, a supersonic wave nozzle, or a method involving adding dropwise the active ingredient solution/dispersion from a tubelike nozzle may be used. When the active ingredient solution/dispersion is added, layering or coating by laminating the active ingredient on the surface of the cellulose powder of the present invention can be performed; or the active ingredient may be retained in the inside of the cellulose powder of the present invention; or a mixture of the cellulose powder of the present invention or a porous cellulose and other additives may be granulated in the form of a matrix using the active ingredient solution/dispersion as a binding liquid. The layering and coating may be applied by a wet process or a dry process.

A mixing method is not particularly limited provided that it is a commonly performed method; a vessel rotation type mixer such as V-type, W-type, double cone type and container tack type mixers, a stirring type mixer such as high speed stirring type, universal stirring type, ribbon type, pug type and Nauta-type mixers, a high speed fluid type mixer, a drum type mixer, and a fluidized bed type mixer may be used. In addition, a vessel shaking type mixer such as a shaker may also be used.

A method for compression molding of the composition is not particularly limited provided that it is a commonly performed method; a method for compressing and molding to form a desired shape with a martor and pestle or a method for compressing and molding to form in advance a sheet to be cut into a desired form may be used. As a compression molding machine, for example, a compressor such as a hydrostatic press, a roller type press such as a briquetting roller type press or a smoothing roller type press, a single-punch tableting machine, or a rotary tableting machine may be used.

A method for dissolving or dispersing the active ingredient in a medium is not particularly limited provided that it is a commonly performed dissolution or dispersion method; a stirring/mixing method using a stirring blade such as one-direction rotation type, multi-axis rotation type, reciprocal inversion type, vertical movement type, rotation+vertical movement type, and piping type such as a portable mixer, a three-dimensional mixer, and a side-wall mixer; a jet type stirring/mixing method such as a line mixer; a gas-blowing stirring/mixing method; a mixing method using a high-shear homogenizer, a high-pressure homogenizer, an ultrasonic homogenizer, or the like; a vessel shaking type mixing method using a shaker, or the like may be used.

A solvent used in the above described production method is not particularly limited provided that it is used in pharmaceutical preparations. For example, water and/or an organic solvent may be used. Examples thereof include ones classified as solvents in "Japanese Pharmaceutical Excipients Directory" (issued by Yakuji Nippo Limited), including alcohols such as methanol, ethanol, isopropyl alcohol, butyl alcohol, 2-methylbutyl alcohol, and benzyl alcohol, hydrocarbons such as pentane, hexane, heptane, and cyclohexane, and ketones such as acetone, and ethyl methyl ketone. These may be freely used alone, or two or more of them may be combined. After dispersing in one type of medium and removing the medium, the dispersion may be carried out with a different medium.

Examples of a water-soluble polymer as a solubility enhancing agent include water-soluble polymers as described in "Japanese Pharmaceutical Excipients Directory" (issued by Yakuji Nippo Limited), including hydroxypropyl cellulose, hydroxypropyl methylcellulose, polyacrylic acid, carboxy vinyl polymer, polyethylene glycol, polyvinyl alcohol, polyvinylpyrrolidone, methylcellulose, ethylcellulose, gum arabic, and starch glue. These may be used alone, or two or more of them may be combined.

Examples of a fat and oil as a solubility enhancing agent include fat and oils as described in "Japanese Pharmaceutical Excipients Directory" (issued by Yakuji Nippo Limited), including monoglyceride stearate, triglyceride stearate, sucrose stearic acid ester, paraffins such as liquid paraffin, carnauba wax, hydrogenated oils such as hydrogenated castor oil, castor oil, stearic acid, stearyl alcohol, and polyethylene glycol. These may be used alone, or two or more of them may be combined.

Examples of a surfactant as a solubility enhancing agent include ones classified as surfactants in "Japanese Pharmaceutical Excipients Directory" (issued by Yakuji Nippo Limited), including phospholipid, glycerin fatty acid ester, polyethylene glycol fatty acid ester, sorbitan fatty acid ester, polyoxyethylene hardened castor oil, polyoxyethylene cetyl ether, polyoxyethylene stearyl ether, polyoxyethylene nonylphenyl ether, polyoxyethylene polyoxypropylene glycol, polyoxyethylene sorbitan monolaurate, polysorbate, sorbitan monooleate, glyceride monostearate, monooxyethylene sorbitan monopalmitate, monooxyethylene sorbitan monostearate, polyoxyethylene sorbitan monooleate, sorbitan monopalmitate, and sodium lauryl sulfate. These may be used alone, or two or more of them may be combined.

As used herein, the composition refers to a mixture of an active ingredient, other additives, and the cellulose powder of the present invention.

As used herein, the molded product refers to one having a form of granules, fine granules, slug, tablets, or the like and comprising the cellulose powder of the present invention, one or more active ingredients, and, if necessary, other additives.

Examples of a method for molding into tablets include, for example, i) a direct compression method which involves directly compressing and molding a mixture of an active ingredient with the cellulose powder of the present invention or a mixture of one or more functional ingredients, with the cellulose powder of the present invention, and, if necessary, other additives, ii) a wet/dry granule compression method which involves mixing and granulating an active ingredient, the cellulose powder of the present invention, and, if necessary, other additives to make granules, and compressing and molding the granules by a conventional method, and iii) a wet/dry granule method with adding a disintegrant which involves mixing and granulating an active ingredient, the cellulose powder of the present invention, and, if necessary, other additives to make granules, further mixing the cellulose powder of the present invention and, if necessary, other additives, and compressing and molding the mixture by a conventional method. Other production methods for a multicore tablet having as an inner core a tablet which is preliminarily compressed and molded, or a multilayer tablet in which a plurality of molded products prepared by preliminary compression are laminated and again compressed, can be used. The direct compression method is preferable in view of productivity and ease of process control.

A method for using the composition comprising one or more active ingredients and the cellulose powder will now be described. The composition of a solid, liquid or semisolid active ingredient and the cellulose powder obtained by the method described above may be used as a solid preparation in a powdery or granular form or used as a coated powdery or granular solid preparation obtained by coating the powdery or granular composition with a coating agent. The coated/uncoated powdery or granular composition obtained here may be used by being packed in capsules or may be used as a tablet-type solid preparation obtained by compressing and molding them. Coating may further be applied on the capsule or tablet for use.

Here, examples of the coating agent for applying coating include coating agents as described in "Japanese Pharmaceutical Excipients Directory" (issued by Yakuji Nippo Limited), including ethyl acrylate methyl methacrylate co-polymer dispersion, acetyl glycerin fatty acid ester, amino alkyl methacrylate copolymer, powdered acacia, ethyl cellulose, ethyl cellulose aqueous dispersion, octyl decyl triglyceride, olive oil, kaolin, cacao butter, prunella spike, caster wax, caramel, carnauba wax, carboxyvinyl polymer, carboxymethyl ethyl cellulose, sodium carboxymethyl starch, carmellose calcium, carmellose sodium, hydrated silicon dioxide, dried aluminum hydroxide gel, dried lactescence bleached lac, dried methacrylic acid copolymer, glutinous rice powder, fish scale powder, gold leaf, silver foil, triethyl citrate, glycerin, fatty acid ester of glycerin, magnesium silicate, light silicic anhydride, hydroxypropylcellulose containing light silicic anhydride, light liquid paraffin, whale wax, crystalline cellulose, hardened oil, synthetic aluminum silicate, synthetic wax, high glucose starch syrup, hard wax, succinylated gelatin, wheat flour, wheat starch, rice starch, cellulose acetate, vinyl acetate resin, cellulose acetate phthalate, white beeswax, titanium oxide, magnesium oxide, dimethylaminoethyl metaacrylate-methyl methacrylate copolymer, dimethylpolysiloxane, dimethylpolysiloxane/silicon dioxide mixture, silicon oxide mixture, plaster, sucrose fatty acid ester, agalloch powder, aluminum hydroxide gel, hydrogenated rosin glycerin ester, stearyl alcohol, stearic acid, aluminum stearate, calcium stearate, polyoxyl stearate, magnesium stearate, purified gelatine, purified shellac, purified sucrose, zein, sorbitan sesquioleate, cetanol, plaster, gelatine, shellac, sorbitan fatty acid ester, D-sorbitol, D-sorbitol liquid, tricalcium phosphate, talc, calcium carbonate, magnesium carbonate, single syrup, middle gold leaf, precipitated calcium carbonate, low substitution degree hydroxypropylcellulose, terpene resin, starch (soluble), corn syrup, corn oil, triacetin, calcium lactate, white shellac, sucrose, honey, hard fat, paraffin, pearl powder, potato starch, hydroxypropylcellulose, hydroxypropylcellulose acetate succinate, hydroxypropylcellulose/titanium oxide/polyethylene glycol mixture, hydroxypropyl methylcellulose phthalate, piperonyl butoxide, castor oil, diethyl phthalate, dibutyl phthalate, blytu phthalyl butyl glycolate, glucose, partially pregelatinized starch, fumaric acid/stearic acid/polyvinylacetal diethylamino acetate/hydroxypropylcellulose mixture, pullulan, propylene glycol, powdered sugar, bentonite, povidone, polyoxyethylene hydrogenated castor oil, polyoxyethylene (105) polyoxypropylene (5) glycol, polyoxyethylene (160) polyoxypropylene (30) glycol, polyoxyethylene sorbitan monostearate, polyvinylacetal diethylamino acetate, polyvinyl alcohol (partially saponified), polyethylene glycol, terminal hydroxyl group substituted methyl polysiloxane silicone resin copolymer, D-mannitol, starch syrup, beeswax, myristyl alcohol, silicic anhydride hydrate, phthalic anhydride, anhydrous calcium hydrogenphosphate, methacrylic acid copolymer, magnesium aluminometasilicate, methyl cellulose, 2-methyl-5-vinylpyridine methylacrylate-methacrylic acid copolymer, vegetable wax, glyceryl monostearate, sorbitan monostearate, sorbitan monolaurate, montanic acid ester wax, pharmaceutical carbon, laumacrogol, calcium sulfate, liquid cumarone resin, liquid paraffin, dl-malic acid, calcium monohydrogen phosphate, calcium hydrogenphosphate, sodium hydrogenphosphate, calcium dihydrogen phosphate, and rosin; these may be used alone, or two or more of them may be combined.

A granulation method used in the production process through granulation step includes dry granulation, wet granulation, heating granulation, spray granulation, and microencapsulation. Specifically, fluidized-bed granulation, stirring granulation, extrusion granulation, crushing granulation and tumbling granulation methods are useful as the wet granulation method. The fluidized-bed granulation method involves performing granulation by spraying a binding liquid on a fluidized powder in a fluidized-bed granulator. The stirring granulation involves simultaneously performing the mixing, kneading and granulation of the powder in a tightly-sealed structure by rotating a stirring blade in a mixing vessel while adding a binding liquid. The extrusion granulation involves performing granulation by forcibly extruding a wet mass kneaded by adding a binding liquid, through a screen in a suitable size by a screw-type or a basket-type method. The crushing granulation method involves performing granulation by shearing and crushing a wet mass kneaded by adding a binding liquid, by the rotary knife of a granulator and sputtering the sheared and crushed matter from the circumferential screen by its centrifugal force. The tumbling granulation method involves performing granulation by tumbling the powder by the centrifugal force of a revolving rotor and forcing spherical granules having a uniform particle size to be grown larger and larger by a binding liquid sprayed from a spray gun at the time of tumbling.

As a method for drying the granulated product, any of a hot-air heating type method (shelf drying, vacuum drying, and fluidized bed drying), a heat type (pan type, shelf box type, and drum type) method and lyophilization can be used. The hot air heating type method involves directly contacting additives with hot air and simultaneously removing evaporated water. The heat conduction type method involves indirectly heating additives through a heat conducting wall. The lyophilization involves freezing additives at −10 to 40° C. and then warming them under high vacuum ($1.3 \times 10^{-5}$ to $2.6 \times 10^{-4}$ MPa) to sublimate and remove water.

A method for adding one or more active ingredients, the cellulose powder of the present invention, other additives, or granules is not particularly limited provided that it is a commonly performed method. These may be continuously added or collectively charged using a small size suction transport apparatus, an air transport apparatus, a bucket conveyor, a pneumatic transport apparatus, a vacuum conveyer, a vibration type quantitative metering feeder, a spray, a funnel, or the like.

The content CV of an active ingredient in the composition and molded product of the present invention which contains 0.1 to 20% by weight of the active ingredient is preferably 5% or less, more preferably 2% or less, particularly preferably 1.5% or less, by adding 0.1 to 50 parts by mass of the cellulose powder of the present invention. The content CV of an active ingredient is represented by the following formula using the average value and standard deviation of the content of the active ingredient in the composition or molded product.

$$CV (\%) = \text{Standard Deviation of Content of Active Ingredient} / \text{Average Value of Content of Active Ingredient} \times 100$$

The cellulose powder of the present invention is also applicable to industrial applications. For example, important functions in the metallurgy field include abrasive resistance, mechanical strength, and machinability. Ingredients fulfilling such functions include an iron-based powder for powder metallurgy. The iron-based powder for powder metallurgy refers to a metal powder such as iron powder. Other additives include alloy powder such as copper powder, graphite powder, and iron phosphide powder; lubricants such as zinc stearate and polyethylene wax; one or more selected from stearic acid, oleic acid monoamide, and stearic acid monoamide; bonding materials such as ethylene bis stearic acid amide, methylene his stearic acid amide, stearic acid, oleic acid amide, stearic acid amide, and a molten mixture of stearic acid amide and ethylene his stearic acid amide; lubricants such as oleic acid, spindle oil, and turbine oil; one or more heat-melted products selected from higher fatty acid, higher fatty acid amide, and wax; talc; metal sulfides; higher fatty acid lithium as a free powder; higher fatty acid amide; and wax. Other materials in an amount of 0.1 to 5% by weight, preferably 0.1 to 2% by weight and the cellulose powder of the present invention in an amount of 0.1 to 50% by weight, preferably 0.1 to 20% by weight may be added to an ingredient fulfilling functions in the metallurgy field, such as an iron-based powder for powder metallurgy. The use of the cellulose powder of the present invention can suppress reductions in sintered strength, mechanical strength, abrasive resistance and machinability due to ununiformity in mixing iron powder for metallurgy, graphite, copper, and the like. A binder is added while mixing an iron-based powder for powder metallurgy and the cellulose powder of the present invention, and the mixture is then vacuum deaired, to which a lubricant and the binder are then added while mixing. After sintering, the mixture preferably has a tensile strength of 140 kg/mm² or more. The separation force for separating the inner and outer sintered portions from each other is preferably 15 tons or more. The sintered metal has abrasive resistance, mechanical strength, and machinability.

An ingredient having gloss and smoothness and effective in eliminating color heterogeneity is important in the powder coating field. Examples of the ingredient include urethane and urea-binding resins as thermosetting resins, vinyl, polyester and epoxy polymer resins which have groups having reactivity with isocyanate groups in the molecular ends, and polyester polymer resins. Other additives include pigments: benzidine yellow, phthalocyanine blue, and permanent red 4R. The cellulose powder of the present invention may be added in an amount of 0.1 to 50% by weight, preferably 0.1 to 20% by weight. Coating methods include a method which involves mixing a pigment, a thermoplastic resin, and the cellulose powder of the present invention and then carrying out temperature control and coating; a method which involves mixing a pigment, a thermoplastic resin, and the cellulose powder of the present invention and then once pulverizing the mixture, followed by temperature control carried out in such a manner that individual pulverized particles do not attach together and coating; and a method which involves mixing the pigment obtained, a thermoplastic resin, and the cellulose powder of the present invention and coating the mixture by spraying in a molten state under a low temperature atmosphere. The coating method includes, but is not particularly limited to, as a common coating method using a powder coating, a fluidized bed coating method, a corona electrical charging method, and an electrostatic coating method such as a triboelectric charging method. The addition of the cellulose powder of the present invention enables uniform blending without producing color heterogeneity. Thus, many types of powder coatings are obtained from a few types of powder coatings, and a composition is obtained which is excellent in thermal stability and can impart stable quality and smooth physical properties to its product because of the small particle size. In addition, in the powder coating filed, when an amorphous secondary aggregate is used as a powder coating, or when a resin having urethane and urea bonds which is a powder coating mixture obtained by dry-blending two or more thermoset powder pigments or a resin in which at least one of thermoset powder pigments contains urethane and urea bonds is used, use of the cellulose powder of the present invention improves the gloss, smoothness, color heterogeneity, and the like.

Further, in industrial molding applications, an ingredient for obtaining strength, rigidity, and toughness is important. Such ingredients include thermoplastic resins. Examples thereof can include polyamide resins, polyphenylene ether resins, polyoxymethylene resins, aromatic polyester resins, aromatic polycarbonate resins, polyphenylene sulfide resins, polyolefin resins, styrene resins, acrylic resins, liquid crystal resins, condensation type resins such as aramid or polyimide, polyether resins such as polysulfone, polyether sulfone or polyether ketone, halogen-containing vinyl compound resins such as polyvinyl chloride, polyvinylidene chloride, polyvinyl fluoride or polyvinylidene fluoride, or rubber. Other added substances are not particularly limited provided that for example, they are inorganic substance powders and known inorganic substances used to reinforce thermoplastic resins. Examples thereof include glass or carbon fiber, calcium silicate fiber, potassium titanate fiber, aluminum borate fiber, glass flake, talc, kaolin, mica, hydrotalcite, calcium carbonate, zinc carbonate, zinc oxide, calcium monohydrogen phosphate, wollastonite, silica, zeolite, alumina, boehmite, aluminum hydroxide, silicon oxide, magnesium oxide, calcium silicate, sodium aluminosilicate, magnesium silicate, Ketjen Black, acetylene black, furnace black, carbon nanotube, graphite, brass, copper, silver, aluminum, nickel, iron, calcium fluoride, mica, montmorillonite, swellable fluorine mica, and apatite. The blending ratio of the cellulose powder of the present invention is 0.1 to 50% by weight, preferably 0.1 to 20% by weight. The production method comprises the steps of: obtaining slurry with a slurry medium containing an inorganic substance powder; grinding the inorganic substance in a slurry state; and mixing the slurry after grinding, a thermoplastic resin, and the cellulose powder of the present invention and removing the slurry medium. The composition comprised of the cellulose powder of the present invention, a thermoplastic resin, and an inorganic substance powder can be applied to automotive parts, industrial parts, electronic parts, gears, and the like; and tubes, rods, filaments, films, blown products in extrusion applications. It is excellent in strength, rigidity, toughness, and appearance. When increased fineness is achieved by grinding in a slurry state to provide an inorganic or organic substance excellent in toughness, appearance, and the like and suitable as a material for various industrial parts in the industrial molding field, use of the cellulose powder of the present invention can provide sufficient strength, rigidity and toughness because it enables uniform dispersion.

An ingredient imparting moldability, bending strength, and surface smoothness is also important in cement or asphalt. Examples of the ingredient include cement. Other added substances include inorganic substance powders, reinforcing fibers, and fluidity-imparting agents. Inorganic substance powders include quartzite fine powder or crystalline inorganic substance powders. The reinforcing fiber is used to improve moldability and the impact strength of a molded product. Examples thereof include defibrated pulp, organic fiber, and polypropylene fiber. Fluidity-imparting agents include cellulosic admixtures. The blending ratio of the cellulose powder of the present invention is preferably 0.1 to 50% by weight, preferably 0.1 to 20% by weight. Production methods include a method which involves mixing cement, the cellulose powder of the present invention, an inorganic substance powder, a reinforcing fiber, and a fluidity-imparting agent and adding water to the mixture, followed by kneading. The cement or asphalt obtained by adding the cellulose powder of the present invention has moldability, bending strength, and surface smoothness. When it is used in a cement composition of which the water content is reduced based on the cement component in the composition, making the composition uniform can suppress an increase in extrusion pressure during extrusion molding, which can contribute to increasing fluidity and enables the deterioration of moldability, bending strength, and surface smoothness produced by friction during the extrusion molding to be avoided.

A coloring agent/pigment is also an important ingredient in the tonner field; other added substances include a binder resin, a charge-controlling agent, and an inorganic fine powder. As the coloring agent/pigment, black pigments include azine pigments, metal salt azo pigments, metal oxides, and combined metal oxides such as carbon black, oil-furnace black, channel black, lamp black, and aniline black. Yellow pigments include cadmium yellow, mineral fast yellow, nickel titanium yellow, naples yellow, naphrol yellow S, hansa yellow G, Hansa yellow 10G, benzine yellow GR, quinoline yellow lake, permanent yellow NCG, and tartrazine lake. Red pigments include iron oxide red, cadmium red, permanent red 4R, linol red, birazolone red, lake red D, brilliant carmin 6B, eosin lake, rhodamine lake B, azarin lake, and brilliant carmin 3B. Blue pigments include cobalt blue, alkali blue, Victoria blue lake, phthalocyanine blue, nonmetal phthalocyanine blue, partially chlorinated phthalocyanine blue, fast sky blue, and indanthrene blue BC. All of these are dry powdered pigments. As the binder resin, vinyl resins include homopolymers of styrene and its substituted products such as polystyrene, poly-P-chlorostyrene, and polyvinyl toluene; styrene copolymers such as styrene-p-chlorostyrene copolymer, styrene-propylene copolymer, styrene-vinyl toluene copolymer, styrene-vinyl naphthalene copolymer, styrene-methyl acrylate copolymer, styrene-ethyl acrylate copolymer, styrene-butyl acrylate copolymer, styrene-octyl acrylate copolymer, styrene-methyl methacrylate copolymer, styrene-ethyl methacrylate copolymer, styrene-butyl methacrylate copolymer, styrene-α-chloromethacrylic acid copolymer, styrene-acrylonitril copolymer, styrene-vinyl methyl ether copolymer, styrene-vinyl ethyl ether copolymer, styrene-maleic acid copolymer, and styrene-maleic acid ester copolymer; polymethyl methacrylate; polybutyl methacrylate; polyvinyl chloride; polyvinyl acetate; epoxide resin; polyamide resin; urethane resin; phenol resin; butyral resin; rosin; modified rosin; and terpene resin. Examples of the epoxy resin include a polycondensate of a bisphenol (e.g., bisphenol A or bisphenol F) and epichlorohydrin. Examples of the charge-controlling agent include nigrosine, azine dyes each containing an alkyl group having 2 to 16 carbons (JP 42-1627 B), basic dyes (e.g., C.I. Basic Yellow 2: C.I. 41000), C.I. Basic Yellow 3, C.I. Basic Red 1, C.I. Basic Red 9: C.I. 42500), C.I. Basic Violet 1: C.I. 42535), C.I. Basic Violet 3: C.I. 42555), C.I. Basic Violet 10: C.I. 45170), C.I. Basic Violet 14: C.I. 42510), C.I. Basic Blue 1: C.I. 42025), C.I. Basic Blue 3: C.I. 51005), C.I. Basic Blue 5: C.I. 42140), C.I. Basic Blue 7: C.I. 42595), C.I. Basic Blue 9: C.I. 52015), C.I. Basic Blue 24: C.I. 52030), C.I. Basic Blue 25: C.I. 52025), and C.I. Basic Green 4: C.I. 42000), lake pigments of these basic dyes, C.I. Solvent Black 8: C.I. 26150), quaternary ammonium salts such as benzoylmethyl-hexadecylammonium chloride and decyltrimethyl chloride, dialkyltin compounds such as dibutyl and dioctyl, dialkyltin borate compounds, guanidine derivatives, polyamine resins such as a vinyl polymer containing an amino group and a condensation-type polymer containing an amino group, metal complexes of monoazo dyes disclosed in JP 41-20153 B, JP 43-27596 B, JP 44-6397 B, and JP 45-26478 B, complexes of metals (Zn, Al, Co, Cr, Fe, and the like) with salicylic acid, a dialkylsalicylic acid, naphthoic acid, and dicarboxylic acid disclosed in JP 55-42752 B and JP 59-7385 B, and a sulphonated copper phthalocyanine pigment. Examples of the inorganic fine powder include one selected from oxides and composite oxides of Si, Ti, Al, Mg, Ca, Sr, Ba, In, Ga, Ni, Mn, W, Fe, Co, Zn, Cr, Mo, Cu, Ag, and V, or a mixture of two or more thereof. Of these, fine powders of silicon dioxide (silica), titanium dioxide and alumina are preferably used. These fine powders may be subjected to surface modification treatment with a hydrophobizing agent or the like. The blending ratio of the cellulose powder of the present invention is 0.1 to 50% by weight, preferably 0.1 to 20% by weight. Production is performed through mix-stirring, kneading, grinding, and sizing. The toner during mixing is less attached to the apparatus and is a composition which less bites into the screw portion of a kneader. When in recovering and recycling a fine powder toner (substandard toner), the cellulose powder of the present invention is used for a method involving directly returning it to the step of mixing raw materials, or a method involving introducing the recovered toner into a granulator to granulate it by applying a predetermined pressure, followed by returning it to the raw material mixing step, the fluidity of a composition containing the functional ingredients such as the color pigment due to the recovered substandard fine powder is reduced to make the dispersibility and uniformity improved, enabling the suppression of the feed neck phenomenon that the biting into the screw portion of a kneader is made poor, in recovering and recycling the substandard fine powder toner generated in the step of sizing a fine powder particularly in a method for producing the toner by mixing, kneading, grinding and sizing a binder resin, a color pigment, and a charge-controlling agent.

Bismuth oxide is an important ingredient in various electronic parts such as a varistor, a ferrite magnet, a battery material, and a piezoelectric material. Other added substances include ZnO, $Sb_2O_3$, $MnO_2$, and CoO. The index of electrical conductivity includes, for example, a varistor $\alpha$ value. The varistor $\alpha$ value refers to an index number of voltage when the relation of voltage and current between both terminals is approximated by proportionality. The blending ratio of the cellulose powder of the present invention is 0.1 to 50% by weight, preferably 0.1 to 20% by weight. The production process involves, for example, wet-mixing raw materials and drying, molding and firing the mixture to provide a pelletized composition. The composition obtained by adding the cellulose powder of the present invention preferably has a varistor $\alpha$ value of 50 or more. In the electronic industry material field, the use of the cellulose powder of the present invention in producing various electronic parts such as a varistor, a ferrite magnet, a battery material, and a piezoelectric material suppresses the segregation of bismuth oxide and enables to stove the problems regarding the stability and persistence of a varistor characteristic value $\alpha$ and electromotive force.

The cellulose powder of the present invention can also be used in the cosmetic field. In the cosmetic field, the uniformity of cosmetic pigments is important for foundations. Cosmetic pigments include inorganic pigments such as talc, mica, sericite, kaolin, bentonite, silica, alumina, magnesium carbonate, barium sulfate, cobalt blue, ultramarine blue, iron blue, manganese violet, titanium-coated mica, bismuth oxychloride, ferric oxide (yellow, red, and black), magnesium oxide, zinc oxide, titanium oxide, zirconium oxide, boron nitride, magnesium aluminosilicate, and aluminum powder, and organic pigments such as acrylic resin, polyester resin, fluororesin, polyethylene resin, Red No. 202, Red No. 204, Red No. 226, Yellow No. 401, and Blue No. 404; further examples thereof include biological polymers such as keratin powder, collagen powder, silk powder, cellulose powder, and chitosan powder. A powder in which these powders are combined can also be used. In addition, the powders of which surface is treated with metal soap, silicone, a perfluoroalkyl, or lecithin may be used. Other added substances which can be used include one of solid oils, liquid oils, and semisolid oils, or a mixture of one or two or more of each oils. Examples thereof include solid fat (wax), hardened oil, liquid paraffin, squalene, squalane, vaseline, polyisobutylene, isopropyl myristate, glyceryl monostearate, coconut oil fatty acid triglyceride, stearyl alcohol, hexadecyl alcohol, palmitic acid, lauric acid, stearic acid, and silicone oil. The blending ratio of the cellulose powder of the present invention is preferably 0.1 to 50% by weight, preferably 0.1 to 20% by weight. As a production process, there is a method which involves mixing a functional ingredient, one or more other added substances, and the cellulose powder of the present invention, mixing an oil phase ingredient comprising a solid oil and/or a liquid oil therein, and grind-mixing and then compressing and molding the resulting mixture. In the mixing, a machine such as a V-type mixer, a ribbon mixer, a Nauter mixer, and a high-speed mixer can be used in addition to a Henschel mixer. The addition of the cellulose powder of the present invention imparts optimal caking properties, spreadability, and adherability. In the case of a foundation, the use of the cellulose powder of the present invention provides a composition excellent in caking, spreadability and feeling, in which a powder ingredient and an oil ingredient are optimally and uniformly mixed in a production method such as involving mixing ingredients such as red iron oxide, yellow iron oxide, black iron oxide, and an ultraviolet absorber and one or more other materials, mixing an oil phase ingredient comprising a solid oil and/or a liquid oil therein, and grind-mixing and then compressing and molding the resulting mixture. In addition, the use of the cellulose powder provides a molded product such as a foundation which is excellent in surface appearance, does not adhere to a cosmetic instrument such as a puff, and has good sense of use. A composition which is hardly cracked in falling and excellent in impact resistance can be made because the strength of its molded product is maintained.

The cellulose powder of the present invention can be applied to the food field. In the food field, for example, the uniformity of ingredients is required such as soy sauce, powdered soy sauce, miso, powdered miso, mash, salted meat, mayonnaise, dressing, vinegar, a sauce of sake, soy, and vinegar, powdered sushi vinegar, chicken bouillon powder, source for tempura, soup for noodles, source, ketchup, sauce for grilled meat, curry paste, stew packet, powdered soup, instant bouillon, seasoning mix, sweet cooking rice wine (mirin in Japanese), new mirin, table syrup, wheat flour, cake flour, egg, chocolate, sugar, fruits, and vegetables. Other added substances include various Japanese cakes such as bean jam and jelly, rice malt, butter cream, custard cream, gum, flour paste, peanut paste, fruit paste, jam, bread crumb, and edible oils such as salad oil. The blending ratio of the cellulose powder of the present invention is 0.1 to 50% by weight, preferably 0.1 to 20% by weight. The production process varies based on the type of food. It comprises the steps of transport, input, filling, and the like. The addition of the cellulose powder of the present invention leads to imparting good taste and a smooth property without lumpy texture.

The present invention will be described with reference to Examples. However, the embodiments of the present invention are not intended to be limited to these Examples. Methods for measuring various physical properties in Examples and Comparative Examples are as follows.

(1) Average Width of Cellulose Primary Particles (μm)

Primary cellulose particles comprising a natural cellulosic material were dried as the need arised, and placed on a sample stage to which a carbon tape was affixed. Vacuum deposition was carried out with platinum palladium (here, a membrane thickness of the deposited membrane was 20 nm or less). Observation was performed at an acceleration voltage of 6 kV and at 250-fold magnification by JSN-5510LV (trade name) from JASCO Corporation. The average value of three typical primary cellulose particles was taken.

(2) Average Thickness of Cellulose Primary Particles (μm)

Primary cellulose particles comprising a natural cellulosic material were dried as the need arised and placed on a sample stage to which a carbon tape was affixed. Vacuum deposition was carried out with gold. The cross section of the cellulose primary particles was cut out with a Ga ion beam using a focused ion beam processing apparatus and then observed at an acceleration voltage of 6 kV and at 1500-fold magnification. The average value of three typical primary cellulose particles was taken.

(3) Average Particle Size of Cellulose Dispersion Particles (μm)

This was defined with 50% cumulative volume of particles in aqueous dispersion of cellulose particles measured by using a laser diffraction particle size distribution analyzer (LA-910 (trade name) from Horiba, Ltd.) under conditions of ultrasonification treatment for 1 minute and a refractive index of 1.20. The measured value does not correlate well with the particle size distribution of dried particles obtained by the following Ro-Tap type apparatus since the measurement principles are totally different from each other. The average particle size measured by laser diffraction is calculated from volume frequencies depending on the major axis of fibrous particles, while the average particle size obtained by the Ro-Tap type depends on the minor axis of fibrous particles because the powder obtained is fractionated by shaking on the sieve. Thus, the measured value by the laser diffraction type depending on the major axis of fibrous particles can be larger than that by the Ro-Tap type depending on the minor axis of fibrous particles.

(4) Crystal Form

X-ray diffraction was carried out using an X-ray diffractometer to determine a crystal form from its X-ray pattern.

(5) Average Particle Size of Dried Cellulose Particles (μm)

The average value of cellulose powders was defined as a particle size of 50% cumulative weight obtained by measuring particle size distribution of a sample of 10 g sieved for 10 minutes with a JIS standard sieve (Z8801-1987) using a Ro-Tap type sieve shaker (Sieve Shaker type A (trade name) from Taira Kosakusho Ltd.).

(6) Bulk Density (g/cm$^3$)

The bulk density was calculated by roughly filling a 25-cm$^3$ metal container with a powder sample over 2 to 3 minutes using a metering feeder or the like, horizontally cutting the top face of the powder layer by abrasion using a hard plate like a knife, measuring the weight of the powder charged in the container, and dividing the measured value by the volume.

(7) Tapping Bulk Density (g/cm$^3$)

Using a commercial powder physical property analyzer (Powder Tester Model T-R (trade name) from Hosokawa Micron Corporation), a 100-cm$^3$ cup was filled with a powder and tapped 180 times. The tapping bulk density was calculated by dividing the weight of the powder layer remaining filled in the cup by the volume of the cup. Since the volume of the powder layer shrinks during tapping compared to that of the cup, a sufficient amount of the powder is placed by attaching an auxiliary column to the cup during the measurement.

(8) Repose Angle

Dynamic self-flowability when a cellulose powder was dropped on a slit at a rate of 3 g/min by a metering feeder was measured with a Sugihara-type repose angle measuring instrument (slit size depth 10×width 50×height 140 mm; a protractor was set at a position of 50 mm in width). The angle between the bottom of the instrument and a layer formed by the cellulose powders is a repose angle.

(9) Specific Surface Area (m$^2$/g)

The specific surface area was measured by BET method with nitrogen as an adsorption gas using TriSTAR (trade name) from Micromeritics. About 1 g of each sample powder was charged and measured. Each sample powder after vacuum drying at 110° C. for 3 hours was used for the measurement.

(10) Internal Frictional Angle (°)

The internal frictional angle was measured using a commercial internal frictional angle measuring instrument (ShearScan TS12 (trade name) from Nihon Rufuto Co., Ltd.). The internal frictional angle when shear stress ($\tau$) was measured in this instrument with a normal stress ($\sigma$) of 3 kPa applied to a sample was used. In this instrument, a straight line (CSL) passing through a steady-state shear value is determined from the failure/collapse line of FIG. 1 and the following formula (1), and the angle (θ) of the straight line CSL is defined as an internal frictional angle:

$$(\tau/c)^n = 1 + (\sigma/\sigma_y) \tag{1}$$

where $\tau$ represents shear stress; $\sigma$ represents normal stress; $\sigma_y$ represents tensile stress; c represents adhesion strength; and n represents a shear exponent.

(11) Observation of Particle Surface Under SEM

Each cellulose sample was placed on a sample stage to which a carbon tape was affixed. Vacuum deposition was carried out with platinum palladium (here, a membrane thickness of the deposited membrane was 20 nm or less). Observation was performed at an acceleration voltage of 6 kV and at 200-1000 fold magnification by JSM-5510LV (trade name) from JASCO Corporation. The sample was determined as positive when having a secondary aggregated particle structure in which primary particles were continuously aggregated, apparently circumscribed, and as negative when forming any other structures.

(12) Reactivity with Drug

Aspirin (official crystal aspirin one-pass treated with a small pulverizer 0.5 mm in diameter) and each cellulose sample are blended by powder-powder in 5/5 (total amount: 0.5 g) in dry process and mixed in glass sample bottle and stored with airtight stopper (60° C.) in an oven (Perfect Oven (trade name) from Tabai Espec) for two weeks and the decomposition ratio is measured. Into a 100 mL measuring flask, 8 g of ferric sulfate (III) sodium 12-hydrate is introduced and pure water is added thereto to make the total 100 mL, which is then used as a color identification test liquid. Into a 50 mL measuring flask, 0.25 g of aspirin after storage (0.5 g for powder blend product) is introduced and ethanol is added thereto to make the total 50 mL, which is then shaken for five minutes. The resultant ethanol solution is filtered and the filtrate is transferred to a 100-mL measuring flask. Ethanol is added thereto to make the total 100 mL. Into a 50-mL measuring flask, 1 ml of this ethanol solution and 1 ml of the above color identification test liquid are introduced, and pure water is added thereto to make the total 50 mL. Absorbance at wavelength 532 nm is measured using an ultraviolet absorbance measuring instrument (from JASCO Corporation). The decomposition ratio is calculated as follows:

Decomposition ratio=(1−(absorbance after storage/absorbance before storage))×100(%)

Those exhibiting a decomposition ratio exceeding 15%, which is the decomposition ratio of aspirin alone, are determined as reactive.

(13) Method for Measuring Acetaminophen Content (Content CV [%])

In the step of mixing acetaminophen, talc or cellulose powder, and other additives as required, the mixer was stopped 5, 15 and 30 minutes after mixing and total 9 samples consisting of 3 samples from the upper layer, the middle layer and the lower layer were taken at each time point using a powder sampler (from Tsutsui Scientific Instruments Co., Ltd., sample volume: 0.8 cm$^3$). Two thousand milligrams was accurately weighed from the sampled powder, placed in a 100-ml measuring flask, and adjusted to 100 ml with purified water. After filtering insoluble matter in the aqueous solution using a resin filter, the content of the drug in the filtrate based on the weight of the sampled powder was quantituted by an optical density method (wavelength: 244 nm). In the case of tablets, one tablet (about 180 mg) was accurately weighed and then quantitation was carried out by a similar operation to calculate the content of the drug contained in one tablet. The average value and standard deviation were calculated for 9 samples in total of the mixed powder and for 10 samples in total of the tablets. The coefficient of variance (also referred to as CV) as a measure of uniformity was determined by the following formula. A lower coefficient of variance indicates a better content uniformity.

Coefficient of Variance (CV) (%)=(Standard Deviation/Average Value)×100

(14) Separation/Segregation Measurement

The apparatus (FIG. 2) has a hopper form in the acrylic frame with 105 cm in width, 73 cm in height and 17.6 cm in depth (the upper and lower portions of the frame is made from iron). The upper width of the hopper is 80.5 cm; the vent is 1 cm in size; and the hopper angle is 60°. A composition is introduced into this separation/segregation-measuring apparatus and the powders at portions of 0, 7, 10, 17, 25, and 27° from the center were sampled. Thereafter, the content of an active ingredient in each sampled powder was quantitated in the same manner as in (13), and the coefficient of variance was calculated in the same manner as in (13).

Example 1

In a low-speed stirrer (from 30LGL reactor (trade name) from Ikebukuro Horo Kogyo Co., Ltd.), 2 kg of a chipped product of a dissolving pulp (19 μm in width and 3 μm in thickness from a broad leaf tree) and 30 L of a 10% hydrochloric acid aqueous solution were placed and hydrolyzed at 105° C. for 30 minutes while stirring to provide an acid-insoluble residue. The resultant acid-insoluble residue was well washed with pure water and then filtered to provide a wet flock (the average particle size of cellulose dispersion particles in this acid insoluble residue was 9.0 μm). The wet flock was introduced into a 90-L plastic bucket and pure water was then added thereto so as to provide a solid content concentration of 6% by weight, followed by neutralization with aqueous ammonia while stirring with a 3-1 motor (pH after neutralization was 7.5 to 8.0). The resultant cellulose dispersion was spray-dried (dispersion supply rate: 6 kg/hr, inlet temperature: 180 to 220° C., outlet temperature: 50 to 70° C., spinning disk diameter: 8 cm, and number of revolutions: 36,000 rpm) to provide a cellulose powder A. Physical properties of the cellulose powder A are shown in Table 1.

Example 2

In a low-speed stirrer (from 30LGL reactor (trade name) from Ikebukuro Horo Kogyo Co., Ltd.), 2 kg of a chipped product of a dissolving pulp (19 μm in width and 3 μm in thickness from a broad leaf tree) and 30 L of a 4N hydrochloric acid aqueous solution were placed and hydrolyzed at 40° C. for 48 hours while stirring to provide an acid-insoluble residue. The resultant acid-insoluble residue was well washed with pure water and then filtered to provide a wet flock. The wet flock was introduced into a 90-L plastic bucket and pure water was then added thereto so as to provide a solid content concentration of 4% by weight, followed by neutralization with aqueous ammonia while stirring with a 3-1 motor (pH after neutralization was 7.5 to 8.0) and quadruple treatments at 70 MPa using a high-pressure homogenizer (RANNIE5-10.38 (trade name) from APV) (The average particle size of cellulose dispersion particles in this acid insoluble residue was 8.1 μm). This was spray-dried (dispersion supply rate: 6 kg/hr, inlet temperature: 180 to 220° C., outlet temperature: 50 to 70° C., spinning disk diameter: 8 cm, and number of revolutions: 30,000 rpm) to provide a cellulose powder B. Physical properties of the cellulose powder B are shown in Table 1.

Example 3

In a low-speed stirrer (from 30LGL reactor (trade name) from Ikebukuro Horo Kogyo Co., Ltd.), 2 kg of a chipped product of a dissolving pulp (19 μm in width and 3 μm in thickness from a broad leaf tree) and 30 L of a 4N hydrochloric acid aqueous solution were placed and hydrolyzed at 40° C. for 48 hours while stirring to provide an acid-insoluble residue. The resultant acid-insoluble residue was well washed with pure water and then filtered to provide a wet flock. The wet flock was introduced into a 90-L plastic bucket and pure water was then added thereto so as to provide a solid content concentration of 2% by weight, followed by neutralization with aqueous ammonia while stirring with a 3-1 motor (pH after neutralization was 7.5 to 8.0) and octuple treatments at 70 MPa using a high-pressure homogenizer (RANNIE5-10.38 (trade name) from APV) (The average particle size of cellulose dispersion particles in this acid insoluble residue was 6.9 μm.) This was spray-dried (dispersion supply rate: 6 kg/hr, inlet temperature: 180 to 220° C., outlet temperature: 50 to 70° C., spinning disk diameter: 8 cm, and number of revolutions: 30,000 rpm) to provide a cellulose powder C. Physical properties of the cellulose powder C are shown in Table 1.

Example 4

In a low-speed stirrer (from 30LGL reactor (trade name) from Ikebukuro Horo Kogyo Co., Ltd.), 2 kg of a chipped product of a dissolving pulp (19 μm in width and 3 μm in thickness from a broad leaf tree) and 30 L of a 10% hydrochloric acid aqueous solution were placed and hydrolyzed at 105° C. for 30 minutes while stirring to provide an acid-insoluble residue. The resultant acid-insoluble residue was well washed with pure water and then filtered to provide a wet flock (the average particle size of cellulose dispersion particles in this acid insoluble residue was 9 μm). The wet flock was introduced into a 90-L plastic bucket and pure water was then added thereto so as to provide a solid content concentration of 8% by weight, followed by neutralization with aqueous ammonia while stirring with a 3-1 motor (pH after neutralization was 7.5 to 8.0). The resultant cellulose dispersion was spray-dried (dispersion supply rate: 6 kg/hr, inlet temperature: 180 to 220° C., outlet temperature: 50 to 70° C., spinning disk diameter: 8 cm, and number of revolutions: 36,000 rpm) to provide a cellulose powder D. Physical properties of the cellulose powder D are shown in Table 1.

Example 5

In a low-speed stirrer (from 30LGL reactor (trade name) from Ikebukuro Horo Kogyo Co., Ltd.), 2 kg of a chipped product of a dissolving pulp (19 μm in width and 3 μm in thickness from a broad leaf tree) and 30 L of a 0.8% hydrochloric acid aqueous solution were placed and hydrolyzed at 130° C. for 50 minutes while stirring to provide an acid-insoluble residue. The resultant acid-insoluble residue was well washed with pure water and then filtered to provide a wet flock (the average particle size of cellulose dispersion particles in this acid insoluble residue was 6 μm). The wet flock was introduced into a 90-L plastic bucket, to which pure water was then added so as to provide a solid content concentration of 4% by weight, followed by neutralization with aqueous ammonia while stirring with a 3-1 motor (pH after neutralization was 7.5 to 8.0). The resultant cellulose dispersion was spray-dried (dispersion supply rate: 6 kg/hr, inlet temperature: 180 to 220° C., outlet temperature: 50 to 70° C., spinning disk diameter: 8 cm, and number of revolutions: 36,000 rpm) to provide a cellulose powder E. Physical properties of the cellulose powder E are shown in Table 1.

Example 6

In a low-speed stirrer (from 30LGL reactor (trade name) from Ikebukuro Horo Kogyo Co., Ltd.), 2 kg of a chipped product of a dissolving pulp (19 μm in width and 3 μm in thickness from a broad leaf tree) and 30 L of a 1.5% hydrochloric acid aqueous solution were placed and hydrolyzed at 135° C. for 90 minutes while stirring to provide an acid-insoluble residue. The resultant acid-insoluble residue was well washed with pure water and then filtered to provide a wet flock (the average particle size of cellulose dispersion particles in this acid insoluble residue was 5 μm). The wet flock was introduced into a 90-L plastic bucket, to which pure water was then added so as to provide a solid content concentration of 4% by weight, followed by neutralization with aqueous ammonia while stirring with a 3-1 motor (pH after neutralization was 7.5 to 8.0). The resultant cellulose dispersion was spray-dried (dispersion supply rate: 6 kg/hr, inlet temperature: 180 to 220° C., outlet temperature: 50 to 70° C., spinning disk diameter: 8 cm, and number of revolutions: 36,000 rpm) to provide a cellulose powder F. Physical properties of the cellulose powder F are shown in Table 1.

Example 7

Mixing and Compression of 1% Acetaminophen Type

Into a 5-L V-type mixer (from Dalton Corporation), 20 g of acetaminophen (from API Co., Ltd., a powder type pulverized product using a small pulverizer, average particle size: 16 μm), 400 g of the cellulose powder A, 400 g of crystalline cellulose "Ceolus" PH-101 (from Asahi Kasei Chemicals Corporation), and 1,180 g of 100-mesh lactose were charged and mixed for 30 minutes (mixing ratio: acetaminophen/cellulose powder A/lactose/crystalline cellulose=1/20/59/20, filling rate: about 65%). This mixture corresponds to Comparative Example 1 of Patent Document 1 in which 2 g of talc is replaced with 400 g of the cellulose powder A, and was adjusted with lactose to make the total mixing ratio 100%. Coefficients of variance of the drug concentrations are shown in Table 2. In Comparative Example 1 of Patent Document 1, due to lack of premixture of talc, the coefficient of variance of the drug concentration is as high as 11.1% even after mixing for 15 minutes, indicating that the speed of mixing is delayed. In contrast, since the cellulose powder of the present invention can be blended in an amount of 20% by weight because of its good dispersibility and low dustability, the speed of mixing can be made rapid. Subsequently, the resultant whole drug-powder mixture was molded into a tablet weighing about 180 mg using a 8-mm-diameter 12R pestle in a rotary tableting machine (LIBRA-II (trade name) from Kikusui Seisakusho Ltd., 12 pestles, rotator diameter: 410 mm) at a turntable rotation rate of 50 rpm. Coefficients of variance of the drug concentrations 10, 30 and 60 minutes after the start of tablet compression are shown in Table 2. The difference between the maximum and minimum values of coefficient of variance was 0.2, indicating that the compression satisfactorily proceeded with little segregation.

Figure 2:
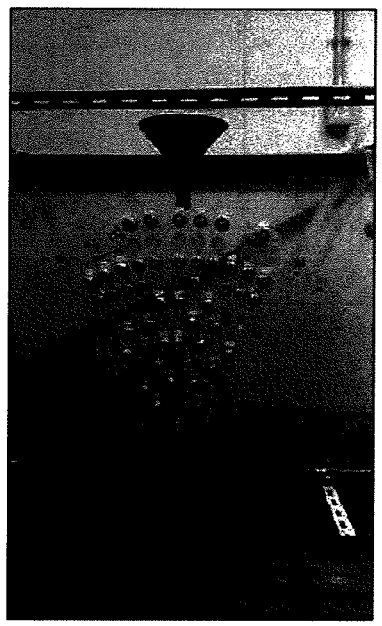
FIG. 2 is a drawing showing an apparatus for measuring separation and segregation.
Figure 3:
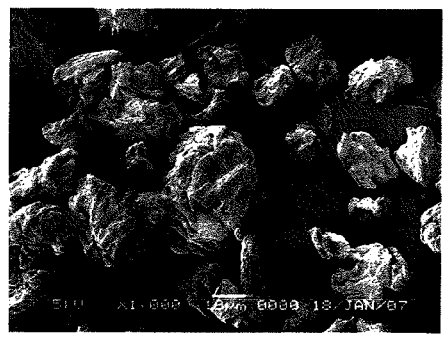
FIG. 3 is a photograph of a cellulose powder A (Example 1) taken at 1,000-fold magnification by a scanning electron microscope (SEM). It shows that this powder is formed of secondary aggregated particles.
Figure 4:
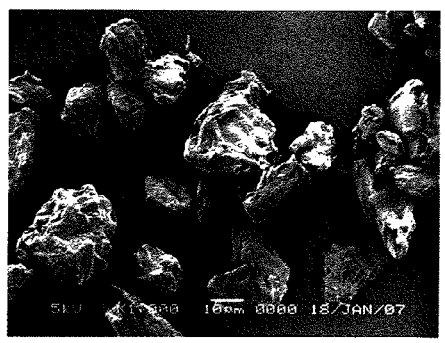
FIG. 4 is a photograph of a cellulose powder B (Example 2) taken at 1,000-fold magnification by a scanning electron microscope (SEM). It shows that this powder is formed of secondary aggregated particles.
Figure 5:
FIG. 5 is a photograph of a cellulose powder E (Example 5) taken at 1,000-fold magnification by a scanning electron microscope (SEM). It shows that primary particles and secondary aggregated particles are present.
Figure 6:
FIG. 6 is a photograph of a cellulose powder E (Example 5) taken at 500-fold magnification by a scanning electron microscope (SEM). It shows that primary particles and secondary aggregated particles are present. The percentage of the secondary aggregated particles was about 76%.
Figure 7:
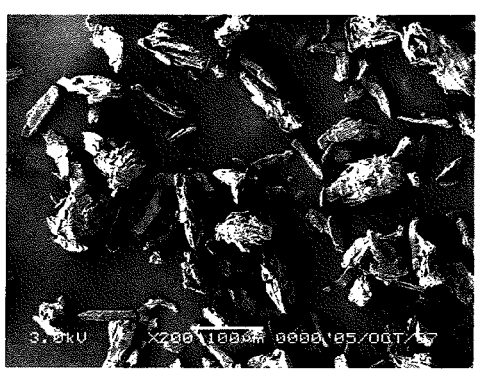
FIG. 7 is a photograph of a cellulose powder G (Comparative Example 2) taken at 200-fold magnification by a scanning electron microscope (SEM). It shows that that primary particles and secondary aggregated particles are present.
Figure 8:
FIG. 8 is a photograph of a cellulose powder I (Comparative Example 4) taken at 200-fold magnification by a scanning electron microscope (SEM). It shows that primary particles and secondary aggregated particles are present.
Figure 9:
FIG. 9 is a photograph of a cellulose powder J (Comparative Example 5) taken at 450-fold magnification by a scanning electron microscope (SEM). It shows that this powder consists only of primary particles.
Figure 10:
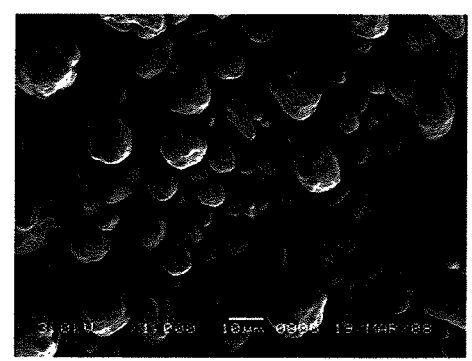
FIG. 10 is a photograph of a cellulose powder L (Comparative Example 7) taken at 1,000-fold magnification by a scanning electron microscope (SEM). It shows that this powder consists only of primary particles.

In the above procedure, the powder mixture obtained by mixing for 30 minute was charged into a separation/segregation-measuring apparatus (see FIG. 2; an acrylic hopper-form conical vessel with 105 cm in width, 73 cm in height and 17.6 cm in depth, in which the width of the powder input section was 80.5 cm, the vent was 1 cm in size, and the conical angle was 60°). The 6 portions of the powder mixture in 0°, 7°, 10°, 17°, 25°, and 27° from the center were sampled. The coefficient of variance of the drug concentration is shown in Table 5. The coefficient of variance of the drug concentration in the conical vessel was lower than that for Comparative Example 1 which uses talc, and thus found to be good.

Examples 8 to 12

The same operations as in Example 7 were followed, except for using cellulose powders B to F in place of cellulose powder A. The results are shown in Table 2. Coefficients of variance of the drug concentrations during mixing and coefficients of variance of the drug concentrations in tablets 10, 30 and 60 minutes after the start of compression are shown in Table 2. The difference between the maximum and minimum values of coefficient of variance was 0 to 0.2 for all samples using the cellulose powder, indicating that the compression satisfactorily proceeded with little segregation.

Example 13

Mixing and Compression of 12% Acetaminophen Type

Into a 5-L V-type mixer (from Dalton Corporation), 240 g of acetaminophen (from API Co., Ltd., used by pulverizing a powder type product using a small pulverizer, average particle size: 16 μm), 200 g of the cellulose powder B, 200 g of crystalline cellulose "Ceolus" KG-802 (from Asahi Kasei Chemicals Corporation; corresponding to that in Example 2 of Patent Document 7), and 1,360 g of spray-dried lactose (Super-Tab (trade name) sold by Asahi Kasei Chemicals Corporation) were charged and mixed for 30 minutes (mixing ratio: acetaminophen/cellulose powder B/lactose/crystalline cellulose=12/10/68/10, filling rate: about 65%). Coefficients of variance of the drug concentrations are shown in Table 3. Subsequently, the resultant powder mixture was molded into a tablet weighing about 180 mg using a 8-mm-diameter 12R pestle in a rotary tableting machine (LIBRA-II (trade name) from Kikusui Seisakusho Ltd., 12 pestles, rotator diameter: 410 mm) at a turntable rotation rate of 50 rpm. Coefficients of variance of the drug concentrations 10, 30 and 60 minutes after the start of tablet compression are shown in Table 3. The difference between the maximum and minimum values of coefficient of variance was 0.1, indicating that the compression satisfactorily proceeded with little segregation.

Example 14

Mixing and Compression of 20% Acetaminophen Type

Into a 5-L V-type mixer (from Dalton Corporation), 400 g of acetaminophen (from API Co., Ltd., used by pulverizing a powder type product using a small pulverizer, average particle size: 16 μm), 200 g of the cellulose powder B, 200 g of crystalline cellulose "Ceolus" KG-802 (from Asahi Kasei Chemicals Corporation), and 1,200 g of spray-dried lactose (Super-Tab (trade name) sold by Asahi Kasei Chemicals Corporation) were charged and mixed for 30 minutes (mixing ratio: acetaminophen/cellulose powder B/lactose/crystalline cellulose=20/10/60/10, filling factor: about 65%). Coefficients of variance of the drug concentrations are shown in Table 4. Subsequently, the resultant powder mixture was molded into a tablet weighing about 180 mg using a 8-mm-diameter 12R pestle in a rotary tableting machine (LIBRA-II (trade name) from Kikusui Seisakusho Ltd., 12 pestles, rotator diameter: 410 mm) at a turntable rotation rate of 50 rpm.

Coefficients of variance of the drug concentrations 10, 30 and 60 minutes after the start of tablet compression are shown in Table 4. The difference between the maximum and minimum values of coefficient of variance was 0.2, indicating that the compression satisfactorily proceeded with little segregation.

Comparative Example 1

Into a 5-L V-type mixer (from Dalton Corporation), 20 g of acetaminophen (from API Co., Ltd., used by pulverizing a powder type product using a small pulverizer, average particle size: 16 μm), 10 g of talc (from Wako Pure Chemical Industries Ltd.), 400 g of crystalline cellulose "Ceolus" PH-101 (from Asahi Kasei Chemicals Corporation), and 1,570 g of 100-mesh lactose were charged and mixed for 30 minutes (corresponding to Comparative Example 1 of Patent Document 1, mixing ratio: acetaminophen/talc/lactose/crystalline cellulose=1/0.5/78.5/20, filling rate: about 65%). Coefficients of variance of the drug concentrations are shown in Table 2. The coefficients of variance of the drug concentration after mixing for 5 minutes and 15 minutes were higher than that of the mixture using the cellulose powder of the present application and thus inferior thereto in terms of the speed of mixing. Subsequently, the resultant powder mixture was molded into a tablet weighing about 180 mg using a 8-mm-diameter 12R pestle in a rotary tableting machine (LIBRA-II (trade name) from Kikusui Seisakusho Ltd., 12 pestles, rotator diameter: 410 mm) at a turntable rotation rate of 50 rpm. Coefficients of variance of the drug concentrations 10, 30 and 60 minutes after the start of tablet compression are shown in Table 2. The difference between the maximum and minimum values of coefficient of variance was 1.1 and thus larger than the mixture using the cellulose powder of the present application, indicating the inferior segregation-suppressing effect thereof.

In a polyethylene bag, 30 g of acetaminophen (from API Co., Ltd., used by pulverizing a powder type product using a small pulverizer, average particle size: 16 μm) and 15 g of talc were placed and mixed by manually shaking for 3 minutes. Then, 30 g of the powder mix, 400 g of crystalline cellulose "Ceolus" PH-101 (from Asahi Kasei Chemicals Corporation), and 1,570 g of 100-mesh lactose were charged into a 5-L V-type mixer (from Dalton Corporation) and mixed for 30 minutes (corresponding to Comparative Example 1 of Patent Document 1, mixing ratio: acetaminophen/talc/lactose/crystalline cellulose=1/0.5/78.5/20, filling rate: about 65%). The coefficient of variance of the drug concentration is shown in Table 5. In addition, the powder mixture mixed for 30 minutes was charged into a separation/segregation-measuring apparatus (see FIG. 2; an acrylic hopper-form conical vessel with 105 cm in width, 73 cm in height and 17.6 cm in depth, in which the width of the powder input section was 80.5 cm; the vent was 1 cm in size; and the angle of the conical angle was 60°). The 6 portions of the powder mixture of 0, 7, 10, 17, 25, and 27° from the center were sampled. The coefficient of variance of the drug concentration is shown in Table 5. The coefficient of variance of the drug concentration in the separation/segregation-measuring apparatus was inferior to the cellulose powder of the present invention.

Comparative Example 2

Two kilograms of a chipped product of a commercial pulp (a wood-derived natural cellulose dissolving pulp, average polymerization degree: 1030, average fiber width of primary cellulose particles: about 39 μm, average thickness: about 8 μm) was immersed in water and passed, with a water content being about 70%, through a cutter mill ("Comitrol" (trade name) Model 1700 from Urschel Laboratories, Inc., microcut head/bladedistance: 2.029 mm, impeller rotation speed: 9,000 rpm), followed by adding pure water thereto to prepare a cellulose dispersion having a concentration of about 2%. The dispersion was treated two times with a high-pressure homogenizer (trade name "Microfluidizer" Model M-140K from MFIC Corp., treatment pressure: 200 MPa) and then centrifuged at a centrifugal force of 19,600 m/s$^2$, followed by discarding the supernatant to provide a precipitate. About 2 kg of a product obtained by drying the precipitate at 40° C. for 16 hours and 30 L of 4N hydrochloric acid aqueous solution were placed in a low-speed stirrer (from 50LGL reactor (trade name) from Ikebukuro Horo Kogyo Co., Ltd.) and hydrolyzed at 40° C. for 48 hours while stirring to provide an acid-insoluble residue. The resultant acid-insoluble residue was washed, filtered, and neutralized to prepare a cellulose dispersion having a solid content concentration of 20% by weight. This dispersion was spray-dried (dispersion feed rate: 6 kg/hr, inlet temperature: 180 to 220° C., outlet temperature: 50 to 70° C.) to provide a cellulose powder corresponding to Example 1 of Patent Document 2. In addition, 75-μm-or-more coarse particles were removed therefrom using a micron separator to provide a cellulose powder G. Physical properties of the cellulose powder G are shown in Table 1.

Comparative Example 3

Two kilograms of a chipped product of a commercial pulp (a wood-derived natural cellulose dissolving pulp, average polymerization degree: 1030, average fiber width of primary cellulose particles: about 39 μm, average thickness thereof: about 8 μm) was immersed in water and passed, with a water content being about 70%, through a cutter mill ("Comitrol" (trade name) Model 1700 from Urschel Laboratories, Inc., microcut head/bladedistance: 2.029, impeller rotation speed: 9,000 rpm), followed by adding pure water thereto to prepare a cellulose dispersion having a concentration of about 2%. The dispersion was treated 4 times with a high-pressure homogenizer (trade name "Microfluidizer" Model M-140K from MFIC Corp., treatment pressure: 200 MPa) and then centrifuged at a centrifugal force of 19,600 m/s$^2$, followed by discarding the supernatant to provide a precipitate. About 2 kg of a product obtained by drying the precipitate at 40° C. for 16 hours and 30 L of 5N hydrochloric acid aqueous solution were placed in a low-speed stirrer (from 50LGL reactor (trade name) from Ikebukuro Horo Kogyo Co., Ltd.) and hydrolyzed at 40° C. for 20 hours while stirring to provide an acid-insoluble residue. The resultant acid-insoluble residue was washed, filtered, and neutralized to prepare a cellulose dispersion having a solid content concentration of 20% by weight. This dispersion was spray-dried (dispersion feed rate: 6 kg/hr, inlet temperature: 180 to 220° C., outlet temperature: 50 to 70° C.) to provide a cellulose powder H corresponding to Example 4 of Patent Document 2. Physical properties of the cellulose powder H are shown in Table 1.

Comparative Example 4

In a low-speed stirrer (50LGL reactor (trade name) from Ikebukuro Horo Kogyo Co., Ltd.), 2 kg of a broad leaf tree was subjected to known pulping and bleaching treatments to provide a pulp of which an average fiber width of primary cellulose particles is about 19 μm, an average thickness is about 3 μm, a level-off polymerization degree is 140 to 220, a water content is 5 to 10%, a whiteness is 92 to 97%, a viscosity is 5 to 40 cps, an S10 is 5 to 15%, an S18 is 1 to 8%, a copper number is 0.5 to 1.5, and a dichloromethane extract is 0.03 ppm or less. In a low-speed stirrer (50LGL reactor (trade name) from Ikebukuro Horo Kogyo Co., Ltd.), 2 kg of the pulp and 30 L of a 5N hydrochloric acid aqueous solution were placed and hydrolyzed at 40° C. for 20 hours while stirring to provide an acid-insoluble residue. The resultant acid-insoluble residue was washed, filtered, and neutralized to prepare a cellulose dispersion having a solid content concentration of 15% by weight. This dispersion was spray-dried (dispersion feed rate: 6 kg/hr, inlet temperature: 180 to 220° C., outlet temperature: 50 to 70° C.) to provide a cellulose powder I corresponding to Example 4 of Patent Document 2. Physical properties of the cellulose powder I are shown in Table 1.

Comparative Example 5

A commercial DP pulp was chipped and hydrolyzed in 10% hydrochloric acid at 105° C. for 20 minutes. The resultant acid-insoluble residue was filtered, washed, dried, and then pulverized with a pneumatic pulverizer (Single Track Jet Mill Model STJ-200 (trade name) from Seishin Enterprise Co. Ltd.) to provide a cellulose powder J corresponding to a sample (C) in Example of Patent Document 3. Physical properties of the resultant cellulose powder J are shown in Table 1.

Comparative Example 6

A commercial DP pulp was chipped and hydrolyzed in 10% hydrochloric acid at 105° C. for 20 minutes. The resultant acid-insoluble residue was filtered, washed, dried, and then pulverized using a pneumatic pulverizer (Single Track Jet Mill Model STJ-200 (trade name) from Seishin Enterprise Co. Ltd.) to provide a cellulose powder K corresponding to a sample (B) in Example of Patent Document 3. Physical properties of the resultant cellulose powder K are shown in Table 1.

Comparative Example 7

One kilogram of rayon lint was chipped and hydrolyzed in a 1.5% hydrochloric acid solution at 130° C. for 50 minutes. The resultant acid-insoluble residue was filtration-washed, spray-dried, and then shredded using ACM Pulverizer. Then, 30-μm-or-more coarse particles were removed therefrom using a micron separator to provide a cellulose powder L corresponding to a sample (D) in Example 1 of Patent Document 4. Physical properties of the resultant cellulose powder L are shown in Table 1.

Comparative Example 8

One kilogram of rayon lint was chipped and hydrolyzed in a 1.5% hydrochloric acid solution at 135° C. for 90 minutes. The resultant acid-insoluble residue was filtration-washed, spray-dried, and then shredded using ACM Pulverizer. Then, 30-micron-or-more coarse particles were removed therefrom using a micron separator to provide a cellulose powder L corresponding to a sample (E) in Example 1 of Patent Document 4. Physical properties of the resultant cellulose powder M are shown in Table 1.

Comparative Example 9

A commercial KP pulp was chipped and hydrolyzed in 10% hydrochloric acid at 105° C. for 20 minutes. The resultant acid-insoluble residue was filtration-washed, air-dried, and then shredded using a conventional hammer mill. A coarse portion was removed using a 50-mesh sieve to provide a cellulose powder N corresponding to Example 3 of Patent Document 5. Physical properties of the resultant cellulose powder N are shown in Table 1.

Comparative Example 10

One kilogram of rayon lint was chipped and hydrolyzed in 1% sulfuric acid at 105° C. for 120 minutes. The resultant acid-insoluble residue was filtration-washed, air-dried, and then shredded using a conventional hammer mill. A coarse portion was removed using a 50-mesh sieve to provide a cellulose powder O corresponding to Example 4 of Patent Document 5. Physical properties of the resultant cellulose powder O are shown in Table 1.

Comparative Example 11

In a high-speed stirring granulator (VG-01 from Powrex Corporation), 1.5 kg of a crystalline cellulose (average polymerization degree: 250) was charged and 900 g of distilled water was added thereto, followed by kneading for 30 minutes. In a coating apparatus of a tumbling flow type, 2.4 kg of the wet granules were charged and tumbled at a charge air temperature of 25° C. for 45 minutes while feeding 340 g of distilled water at a speed of 7.8 g/min., followed by further tumbling for 30 minutes. The granules were then dried by increasing the charge air temperature to 100° C. After drying, they were sieved with a 75 μm opening and a 45 μm opening of a sieve to provide a cellulose P corresponding to Example 3 of Patent Document 6 (of which an average particle size is the closest to the cellulose powder of the present application). Physical properties of the resultant cellulose powder P are shown in Table 1.

Comparative Example 12

Two kilograms of a commercial SP pulp (polymerization degree: 790, level-off polymerization degree: 220) was chipped, placed in 30 L of a 4N hydrochloric acid aqueous solution, and hydrolyzed at 40° C. for 48 hours while stirring using a low-speed stirrer (30LGL reactor (trade name) from Ikebukuro Horo Kogyo Co., Ltd., blade diameter: 30 cm). The resultant acid-insoluble residue was filtered and washed to prepare a cellulose dispersion having a solid content concentration of 8%. This dispersion was spray-dried (liquid feed rate: 6 L/hr, inlet temperature: 180 to 220° C., outlet temperature: 50 to 70° C.) to provide a cellulose powder Q corresponding to Example 2 of Patent Document 7. Physical properties of the resultant cellulose powder Q are shown in Table 1.

Comparative Example 13

The same operations as in Comparative Example 12 were followed, except for using a commercial SP pulp (polymerization degree: 870, level-off polymerization degree: 220) as a pulp and setting hydrolysis conditions to a 3N hydrochloric acid aqueous solution, 40° C., and 24 hours, to provide a cellulose powder R corresponding to Example 6 of Patent Document 7. Physical properties of the resultant cellulose powder R are shown in Table 1.

Comparative Example 14

Two kilograms of a commercial SP pulp was chipped, placed in a 0.5% hydrochloric acid aqueous solution (30 L), and hydrolyzed at 121° C. for one hour while stirring using a low-speed stirrer (from Ikebukuro Horo Kogyo Co., Ltd.). The resultant acid-insoluble residue was vacuum-dried at 70° C., followed by removing a coarse portion using a 325-mesh sieve to provide a cellulose powder S corresponding to Example 1 of JP 40-26274 B. Physical properties of the resultant cellulose powder S are shown in Table 1.

Comparative Example 15

The cellulose powder S was sieved using a 38-μm sieve to provide a cellulose powder T. Physical properties of the resultant cellulose powder T are shown in Table 1.

Comparative Examples 16 to 29

The same operations as in Example 7 were followed, except for using any of cellulose powders G to T in place of cellulose powder A. The results are shown in Table 2. Coefficients of variance of the drug concentrations during mixing and coefficients of variance of the drug concentrations in tablets 10, 30 and 60 minutes after the start of compression are shown in Table 2. With regard to each of the cellulose powders, a coefficient of variance of the drug concentration after mixing for 30 minutes was not as low as 2% or less, and was inferior to the cellulose powder of the present application. A powder mixture mixed for 30 minutes with any of cellulose powders K, L, M and O was charged into a separation/segregation-measuring apparatus (see FIG. 2; an acrylic hopper-form conical vessel with 105 cm in width, 73 cm in height and 17.6 cm in depth, in which the width of the powder input section was 80.5 cm; the vent was 1 cm in size; and the angle of the conical angle was 60°). The 6 portions of the powder mixture of 0, 7, 10, 17, 25, and 27° from the center were sampled. Coefficients of variance of the drug concentrations are shown in Table 5. Each of the powder mixtures had a high coefficient of variance of the drug concentration and was inferior to that in Example 7 which uses the cellulose powder of the present application.

Comparative Examples 30 to 37

The same operations as in Example 13 were followed, except for using talc or any of cellulose powders G, J, M, N, P, Q, and S in place of cellulose powder B. The results are shown in Table 3. With regard to each of the cellulose powders, a coefficient of variance of the drug concentration after mixing for 30 minutes is not as low as 2% or less, and was inferior to the cellulose powder of the present application.

Comparative Examples 38 to 45

The same operations as in Example 14 were followed, except for using talc or any of cellulose powders G, J, M, N, P, Q, and S in place of cellulose powder B. The results are shown in Table 3. With regard to each of the cellulose powders, a coefficient of variance of the drug concentration after mixing for 30 minutes is not as low as 2% or less, and was inferior to the cellulose powder of the present application.

TABLE 1

| | | | Physical Properties of Cellulose Dispersion | | | Particle Structure | | | | | | | | | Powder Physical Properties of Cellulose Powder |
|---|---|---|---|---|---|---|---|---|---|---|---|---|---|---|---|
| | | Cellulose Powder | Average Particle Size [μm] | Solid Content Concentration [wt %] | Reactivity with Drug | Observed under SEM (Secondary Aggregation Structure) | Crystal Form | Average Particle Size [μm] | Bulk Density [g/cm³] | Tapping Bulk Density [g/cm³] | Repose Angle [°] | BET Specific Surface Area [m²/g] | Internal Frictional Angle [°] | Load at Breakage of 10 Mpa Compression-Molded Product (N) |
| Examples | 1 | A | 8.3 | 6 | No | Positive | I | 26 | 0.31 | 0.41 | 42 | 5.0 | 36.6 | 32 |
| | 2 | B | 8.1 | 4 | No | Positive | I | 20 | 0.28 | 0.36 | 44 | 15.0 | 38.5 | 32 |
| | 3 | C | 6.9 | 2 | No | Positive | I | 15 | 0.39 | 0.45 | 49 | 18.0 | 41.0 | 35 |
| | 4 | D | 16 | 8 | No | Positive | I | 29 | 0.27 | 0.34 | 43 | 0.5 | 39.0 | 45 |
| | 5 | E | 16 | 4 | No | Positive | I | 20 | 0.25 | 0.43 | 48 | 1.3 | 37.0 | 35 |
| | 6 | F | 5 | 8 | No | Positive | I | 10 | 0.15 | 0.48 | 46 | 2.0 | 36.1 | 21 |
| Comparative Examples | 2 | G | 38 | 20 | No | Positive | I | 38 | 0.26 | 0.35 | 42 | 0.8 | 39.0 | 90 |
| | 3 | H | 31 | 20 | No | Positive | I | 31 | 0.33 | 0.45 | 28 | 5.0 | 20.0 | 52 |
| | 4 | I | 35 | 15 | No | Positive | I | 90 | 0.29 | 0.40 | 34 | 1.4 | 32.0 | 62 |
| | 5 | J | Not Slurried | | No | Negative | I | 28 | 0.18 | 0.43 | 57 | 1.4 | 45.6 | 80 |
| | 6 | K | Not Slurried | | No | Negative | I | 12 | 0.11 | 0.38 | 65 | 2.5 | 48.0 | 85 |
| | 7 | L | 9 | 4 | No | Negative | I | 9 | 0.46 | 0.55 | 55 | 0.3 | 35.7 | 12 |
| | 8 | M | 5 | 2 | No | Negative | I | 2 | 0.47 | 0.56 | 60 | 0.8 | 32.2 | 13 |
| | 9 | N | Not Slurried | | No | Positive | I | 32 | 0.51 | 0.63 | 35 | 0.8 | 43.0 | 33 |
| | 10 | O | Not Slurried | | No | Positive | I | 20 | 0.71 | 0.76 | 34 | 0.5 | 32.0 | 20 |
| | 11 | P | Not Slurried | | No | Positive | I | 57 | 0.60 | 0.84 | 33 | 0.1 | 30.5 | 4 |
| | 12 | Q | 44 | 8 | No | Positive | I | 45 | 0.21 | 0.37 | 48 | 1.2 | 43.0 | 80 |
| | 13 | R | 49 | 6 | No | Positive | I | 38 | 0.16 | 0.30 | 54 | 1.7 | 45.0 | 100 |
| | 14 | S | 33 | 17 | No | Positive | I | 40 | 0.32 | 0.43 | 44 | 1.0 | 42.6 | 53 |
| | 15 | T | 33 | 17 | No | Positive | I | 26 | 0.29 | 0.44 | 49 | 1.0 | 43.0 | 38 |

TABLE 2

|  | Cellulose Powder | Coefficient of Variance of Drug Concentration During Mixing [%] | | | | | |
|---|---|---|---|---|---|---|---|
|  |  | 5 min. after | 15 min. after | 30 min. after | 10 min. after | 30 min. after | 60 min. after |
| Example 7 | A | 3.0 | 1.8 | 1.4 | 0.5 | 0.7 | 0.6 |
| Example 8 | B | 1.5 | 1.4 | 1.0 | 0.5 | 0.5 | 0.5 |
| Example 9 | C | 2.0 | 1.4 | 1.2 | 0.6 | 0.7 | 0.5 |
| Example 10 | D | 2.5 | 1.5 | 1.5 | 0.9 | 0.9 | 0.8 |
| Example 11 | E | 2.5 | 1.6 | 1.4 | 0.8 | 0.6 | 0.7 |
| Example 12 | F | 3.6 | 2.0 | 1.5 | 1.0 | 1.2 | 1.1 |
| Comparative Example 1 | - (Talc) | 6.0 | 5.5 | 1.4 | 1.1 | 1.9 | 2.2 |
| Comparative Example 16 | G | 18.5 | 11.1 | 2.2 | 2.2 | 2.3 | 2.1 |
| Comparative Example 17 | H | 7.4 | 5.3 | 2.4 | 2.5 | 2.8 | 2.9 |
| Comparative Example 18 | I | 15.0 | 8.0 | 2.5 | 2.3 | 2.7 | 2.5 |
| Comparative Example 19 | J | 20.3 | 14.5 | 5.2 | Not Possible to Compress | | |
| Comparative Example 20 | K | 25.0 | 18.4 | 9.3 | Not Possible to Compress | | |
| Comparative Example 21 | L | 13.2 | 7.5 | 4.3 | Not Possible to Compress | | |
| Comparative Example 22 | M | 11.3 | 9.0 | 5.2 | Not Possible to Compress | | |
| Comparative Example 23 | N | 13.2 | 6.5 | 2.4 | 2.1 | 2.4 | 2.5 |
| Comparative Example 24 | O | 15.1 | 7.5 | 3.1 | 2.8 | 2.3 | 3.1 |
| Comparative Example 25 | P | 16.7 | 10.3 | 3.5 | 3.1 | 4.1 | 3.5 |
| Comparative Example 26 | Q | 16.3 | 11.2 | 3.8 | 3.5 | 4.2 | 3.6 |
| Comparative Example 27 | R | 18.9 | 13.6 | 4.2 | 3.1 | 3.3 | 4.4 |
| Comparative Example 28 | S | 14.5 | 9.2 | 2.8 | 2.2 | 2.9 | 2.4 |
| Comparative Example 29 | T | 8.2 | 5.2 | 2.5 | 2.6 | 2.2 | 2.9 |

TABLE 3

|  | Cellulose Powder | Coefficient of Variance of Drug Concentration During Mixing [%] | | | | | |
|---|---|---|---|---|---|---|---|
|  |  | 5 min. after | 15 min. after | 30 min. after | 10 min. after | 30 min. after | 60 min. after |
| Example 13 | B | 4.1 | 3.5 | 1.8 | 1.5 | 1.4 | 1.5 |
| Comparative Example 30 | - (Talc) | 6.9 | 2.4 | 3.6 | 2.9 | 4.2 | 2.4 |
| Comparative Example 31 | G | 16.3 | 8.9 | 3.4 | 2.4 | 2.8 | 3.1 |
| Comparative Example 32 | J | 19.1 | 16.2 | 4.9 | Not Possible to Compress | | |
| Comparative Example 33 | M | 13.3 | 6.5 | 4.4 | Not Possible to Compress | | |
| Comparative Example 34 | N | 14.2 | 7.9 | 3.4 | 2.9 | 3.5 | 3.1 |
| Comparative Example 35 | P | 20.1 | 15.6 | 5.1 | 4.3 | 3.7 | 4.5 |
| Comparative Example 36 | Q | 19.2 | 8.8 | 3.1 | 2.6 | 2.7 | 2.1 |
| Comparative Example 37 | S | 15.4 | 7.4 | 2.9 | 2.4 | 3.1 | 2.9 |

TABLE 4

|  | Cellulose Powder | Coefficient of Variance of Drug Concentration During Mixing [%] | | | | | |
|---|---|---|---|---|---|---|---|
|  |  | 5 min. after | 15 min. after | 30 min. after | 10 min. after | 30 min. after | 60 min. after |
| Example 14 | B | 2.3 | 1.5 | 1.0 | 0.8 | 0.6 | 0.6 |
| Comparative Example 38 | - (Talc) | 21.0 | 8.9 | 3.5 | 3.1 | 3.2 | 3.5 |

TABLE 4-continued

| | Cellulose Powder | Coefficient of Variance of Drug Concentration During Mixing [%] | | | | | |
|---|---|---|---|---|---|---|---|
| | | 5 min. after | 15 min. after | 30 min. after | 10 min. after | 30 min. after | 60 min. after |
| Comparative Example 39 | G | 26.9 | 15.4 | 6.3 | 5.3 | 4.8 | 4.4 |
| Comparative Example 40 | J | 28.0 | 15.8 | 7.3 | Not Possible to Compress | | |
| Comparative Example 41 | M | 31.5 | 16.9 | 8.1 | Not Possible to Compress | | |
| Comparative Example 42 | N | 21.0 | 7.7 | 4.5 | 3.1 | 4.2 | 2.9 |
| Comparative Example 43 | P | 29.0 | 14.0 | 6.5 | 5.0 | 4.9 | 5.5 |
| Comparative Example 44 | Q | 24.5 | 10.2 | 5.6 | 4.2 | 4.5 | 5.3 |
| Comparative Example 45 | S | 20.0 | 7.3 | 3.8 | 2.5 | 3.2 | 2.9 |

TABLE 5

| | Cellulose Powder | Coefficient of Variance of Drug Concentration After Mixing for 30 minutes [%] | Coefficient of Variance of Drug Concentration at 6 Portions of Conical Vessel [%] |
|---|---|---|---|
| Example 7 | B | 1.4 | 0.7 |
| Comparative Example 1 | - (Talc) | 1.4 | 2.0 |
| Comparative Example 20 | K | 9.3 | 7.4 |
| Comparative Example 21 | L | 4.3 | 4.5 |
| Comparative Example 22 | M | 5.2 | 4.6 |
| Comparative Example 24 | O | 3.1 | 4.4 |

The invention claimed is:

1. A type I crystalline cellulose powder having an average particle size of 28 μm or less, a bulk density of 0.1 to 0.45 g/cm$^3$, a tapping density of 0.1 to 0.5 g/cm$^3$, a repose angle of 35° to 50°, a specific surface area of greater than or equal to 0.1 and less than 20 m$^2$/g, and an internal frictional angle of 36 to 42°.

2. The cellulose powder according to claim 1, wherein the cellulose powder comprises particle aggregates.

3. The cellulose powder according to claim 2, wherein 10 to 100% by weight of the powder is aggregated.

4. A composition comprising one or more active ingredients and the cellulose powder according to claim 1.

5. The composition according to claim 4, wherein the active ingredient is an active ingredient for pharmaceuticals.

6. The composition according to claim 4, wherein the active ingredient is an active ingredient for health food.

7. The composition according to claim 5, wherein the active ingredient for pharmaceuticals or the active ingredient for health food is an ingredient that chemically reacts with a metal salt.

8. A method for producing a molded product, comprising directly compressing a composition according to claim 4.

9. A method for producing the cellulose powder according to claim 1, comprising:
   obtaining an aqueous dispersion in which an average particle size of a natural cellulosic material is 1 to 20 μm and a solid content concentration of 20% by weight or less; and
   spray-drying the dispersion at a rotator speed of 40 to 200 msec.

10. The method for producing a cellulose powder according to claim 9, wherein the natural cellulosic material is obtained by hydrolyzing pulp fibers having an average thickness of 0.5 to 5 μm.

* * * * *

UNITED STATES PATENT AND TRADEMARK OFFICE
CERTIFICATE OF CORRECTION

PATENT NO.        : 9,132,195 B2
APPLICATION NO.   : 12/993580
DATED             : September 15, 2015
INVENTOR(S)       : Y. Honda et al.

Page 1 of 1

It is certified that error appears in the above-identified patent and that said Letters Patent is hereby corrected as shown below:

In the Claims
Column 42, line 40 (claim 9, line 8) please change "msec." to -- m/sec. --

Signed and Sealed this
Fifth Day of July, 2016

Michelle K. Lee
*Director of the United States Patent and Trademark Office*